(12) United States Patent
Smith et al.

(10) Patent No.: US 11,390,910 B2
(45) Date of Patent: Jul. 19, 2022

(54) METHOD

(71) Applicant: Oxford Nanopore Technologies PLC, Oxford (GB)

(72) Inventors: Nicholas Antony Smith, Oxford (GB); Daniel John Turner, Oxford (GB); Daniel George Fordham, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 455 days.

(21) Appl. No.: 16/343,580

(22) PCT Filed: Oct. 20, 2017

(86) PCT No.: PCT/GB2017/053177
§ 371 (c)(1),
(2) Date: Apr. 19, 2019

(87) PCT Pub. No.: WO2018/073604
PCT Pub. Date: Apr. 26, 2018

(65) Prior Publication Data
US 2019/0249231 A1    Aug. 15, 2019

(30) Foreign Application Priority Data
Oct. 21, 2016  (GB) .................... 1617886

(51) Int. Cl.
| | | |
|---|---|---|
| *C12Q 1/6825* | (2018.01) | |
| *C12Q 1/6816* | (2018.01) | |
| *C12Q 1/68* | (2018.01) | |
| *C12Q 1/6876* | (2018.01) | |

(52) U.S. Cl.
CPC ............. *C12Q 1/6825* (2013.01); *C12Q 1/68* (2013.01); *C12Q 1/6816* (2013.01); *C12Q 1/6876* (2013.01); *C12Q 2525/101* (2013.01); *C12Q 2525/161* (2013.01); *C12Q 2537/143* (2013.01); *C12Q 2563/116* (2013.01); *C12Q 2565/607* (2013.01); *C12Q 2565/631* (2013.01)

(58) Field of Classification Search
CPC ...... C12Q 1/6825; C12Q 1/6816; C12Q 1/68; C12Q 1/6876
See application file for complete search history.

(56) References Cited

U.S. PATENT DOCUMENTS

| | | | | |
|---|---|---|---|---|
| 2005/0272075 A1* | 12/2005 | Jacobsen | ............ | C12Q 1/6816 435/6.18 |
| 2009/0162840 A1 | 6/2009 | Fredriksson et al. | | |

FOREIGN PATENT DOCUMENTS

| | | |
|---|---|---|
| WO | WO 2000/28312 | 5/2000 |
| WO | WO 2006/100484 A2 | 9/2006 |
| WO | WO 2008/102120 A1 | 8/2008 |
| WO | WO 2009/077734 A2 | 6/2009 |
| WO | WO 2010/062903 A2 | 6/2010 |
| WO | WO 2010/086602 A1 | 8/2010 |
| WO | WO 2011/067559 A1 | 6/2011 |
| WO | WO 2012/107778 A2 | 8/2012 |
| WO | WO 2013/121201 A1 | 8/2013 |
| WO | WO 2013/153359 A1 | 10/2013 |
| WO | WO 2014/072703 A1 | 5/2014 |
| WO | WO 2016/034591 A2 | 3/2016 |

OTHER PUBLICATIONS

Van Ravesteyn et al, LNA modification of single-stranded DNA oligonucleotides allows subtle gene modification in mismatch-repair-proficient cells, 2016, 113, 4122-4127. (Year: 2016).*
Altschul et al. Basic local alignment search tool. J Mol Biol. Oct. 5, 1990;215(3):403-10. doi: 10.1016/50022-2836(05)80360-2.
Altschul SF. A protein alignment scoring system sensitive at all evolutionary distances. J Mol Evol. Mar. 1993:36(3):290-300. doi: 10.1007/BF00160485.
Anderson, NL. The clinical plasma proteome: a survey of clinical assays for proteins in plasma and serum. Clin Chem. Feb. 2010;56(2):177-85. doi: 10.1373/clinchem.2009.126706. Epub Nov. 2, 2009.

(Continued)

*Primary Examiner* — Narayan K Bhat
(74) *Attorney, Agent, or Firm* — Wolf, Greenfield & Sacks, P.C.

(57) ABSTRACT

A method for determining the presence, absence or amount of two or more target polynucleotides in a sample comprising additional components, the method comprising: (i) contacting the sample with a panel of two or more probes under conditions suitable for hybridisation of the target polynucleotides to the probes, wherein: (a) each probe comprises a non-hybridisation region and a hybridisation region that specifically hybridises to one of the target polynucleotides to form a hybridised probe; and (b) the hybridisation region of a probe of the panel comprises one or more non-natural nucleotides; (ii) contacting the sample prepared in step (i) with a transmembrane pore through which a single stranded polynucleotide but not a double stranded polynucleotide can pass and applying a potential difference to the transmembrane pore such that the hybridised probes in the sample interact with the pore; (iii) measuring current blockades having a duration within a defined window, wherein: (a) the one or more non-natural nucleotides present in the hybridisation region of the probe increase or decrease the duration of the current blockade due to the probe hybridised to its target polynucleotide such that the proportion of current blockades that occur within the window due to the interaction of the hybridised probes with the pore is increased compared to when the corresponding one or more natural nucleotides are present in the hybridisation region; and (b) each hybridised probe gives rise to a current blockade indicative of that probe; and (iv) correlating the measured current blockades with the probes, thereby determining the presence, absence or amount of the two or more target polynucleotides in the sample.

20 Claims, 4 Drawing Sheets

Specification includes a Sequence Listing.

(56) References Cited

OTHER PUBLICATIONS

Braha et al., Designed protein pores as components for biosensors. Chem Biol. Jul. 1997:4(7):497-505.

Devereux et al., A comprehensive set of sequence analysis programs for the VAX. Nucleic Acids Res. Jan. 11, 1984:12(1 Pt l):387-95. doi: 10.1093/nar/12.1partl.387.

Edwards et al., The role of proteomics in clinical cardiovascular biomarker discovery. Mol Cell Proteomics. Oct. 2008;7(10):1824-37. doi: 10.1074/mcp.R800007-MCP200. Epub Jul. 30, 2008.

Heron et al., Simultaneous measurement of ionic current and fluorescence from single protein pores. J Am Chem Soc. Feb. 11, 2009;131(5):1652-3. doi: 10.1021/ja808128s.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007. Supplementary Info, 6 pages.

Jacquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.

Jiang et al., miR2Disease: a manually curated database for microRNA deregulation in human disease. Nucleic Acids Res. Jan. 2009;37(Database issue):D98-104. doi: 10.1093/nar/gkn714. Epub Oct. 15, 2008.

Kankia et al., Folding of the thrombin aptamer into a G-quadruplex with Sr(2+): stability, heat, and hydration. J Am Chem Soc. Nov. 7, 2001;123(44):10799-804. doi: 10.1021/ja010008o.

Kozarewa et al., 96-plex molecular barcoding for the Illumina Genome Analyzer. Methods Mol Biol. 2011;733:279-98. doi: 10.1007/978-1-61779-089-8_20.

Kumar et al., Nonradioactive labeling of synthetic oligonucleotide probes with terminal deoxynucleotidyl transferase. Anal Biochem. Mar. 1988;169(2):376-82. doi: 10.1016/0003-2697(88)90299-0. Erratum in: Anal Biochem Sep. 1988;173(2):469.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Marathias et al., Structures of the potassium-saturated, 2:1, and intermediate, 1:1, forms of a quadruplex DNA. Nucleic Acids Res. May 1, 2000;28(9):1969-77. doi: 10.1093/nar/28.9.1969.

Marusic et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.

Nikolov et al., Behavior of giant vesicles with anchored DNA molecules. Biophys J. Jun. 15, 2007;92(12):4356-68. doi: 10.1529/biophysj.106.100032. Epub Mar. 23, 2007.

Pfeiffer et al., Bivalent cholesterol-based coupling of oligonucleotides to lipid membrane assemblies. J Am Chem Soc. Aug. 25, 2004;126(33):10224-5.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/1a904822f.

Yoshina-Ishii et al., Arrays of mobile tethered vesicles on supported lipid bilayers. J Am Chem Soc. Apr. 2, 2003;125(13):3696-7. doi: 10.1021/ja029783+.

\* cited by examiner

SEQUENCE LISTING

```
<160> NUMBER OF SEQ ID NOS: 37

<210> SEQ ID NO 1
<211> LENGTH: 75
<212> TYPE: DNA
<213> ORGANISM: Artificial Sequence
<220> FEATURE:
<223> OTHER INFORMATION: Quadruplex-forming sequence

<400> SEQUENCE: 1
tttttttttt cttttttttt cttttttggt tggtgtggtt ggttttttttt accccctatca    60 cgattagcat taatt                                                      75

<210> SEQ ID NO 2
<211> LENGTH: 885
<212> TYPE: DNA
<213> ORGANISM: Artificial Sequence
<220> FEATURE:
<223> OTHER INFORMATION: Polynucleotide sequence encoding one monomer of
      alpha-hemolysin-E111N/K147N (NN)

<400> SEQUENCE: 2
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct    300 gattactatc caagaaattc gattgataca aaaaactata tgagtacttt aacttatgga   360
ttcaacggta atgttactgg tgatgataca ggaaaaattg gcggccttat tggtgcaaat   420
gtttcgattg gtcatacact gaactatgtt caacctgatt tcaaaacaat tttagagagc   480
ccaactgata aaaagtagg ctggaaagtg atatttaaca atatggtgaa tcaaaattgg   540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaatatac gaacgagttc gtgatgatta ccaattgcat   780
tggacttcaa caaattggaa aggtaccaat actaaagata aatggacaga tcgttcttca   840
gaaagatata aatcgattg ggaaaaagaa gaaatgacaa attaa                     885

<210> SEQ ID NO 3
<211> LENGTH: 293
<212> TYPE: PRT
<213> ORGANISM: Artificial Sequence
<220> FEATURE:
<223> OTHER INFORMATION: One monomer of alpha-hemolysin-NN

<400> SEQUENCE: 3

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30
```

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

```
<210> SEQ ID NO 4
<211> LENGTH: 84
<212> TYPE: DNA
<213> ORGANISM: Artificial Sequence
<220> FEATURE:
<223> OTHER INFORMATION: 150_4G1C_1Alt
<220> FEATURE:
<221> NAME/KEY: misc_feature
<223> OTHER INFORMATION: cholesterol TEG at 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (67)..(67)
<223> OTHER INFORMATION: 2'-O-methylRNA
<220> FEATURE:
<221> NAME/KEY: modified_base
<222> LOCATION: (69)..(69)
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
```

<221> NAME/KEY: modified_base
<222> LOCATION: (73)..(73)
<223> OTHER INFORMATION: 2'-O-methylRNA
<220> FEATURE:
<221> NAME/KEY: modified_base
<222> LOCATION: (75)..(75)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (79)..(79)
<223> OTHER INFORMATION: 2'-O-methylRNA
<220> FEATURE:
<221> NAME/KEY: modified_base
<222> LOCATION: (81)..(81)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA

<400> SEQUENCE: 4
tttttttttt cttttttttt tcttttttttt ttcttttttt tttctttttt ttttcttttc    60
ggggcactgg uacaagggut ggga                                            84

<210> SEQ ID NO 5
<211> LENGTH: 84
<212> TYPE: DNA
<213> ORGANISM: Artificial Sequence
<220> FEATURE:
<223> OTHER INFORMATION: 150_4G1C_2Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (68)..(68)
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
<221> NAME/KEY: modified_base
<222> LOCATION: (74)..(74)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (80)..(80)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA

<400> SEQUENCE: 5
tttttttttt cttttttttt tcttttttttt ttcttttttt tttctttttt ttttcttttc    60
ggggcacugg uacaagggtu ggga                                            84

<210> SEQ ID NO 6
<211> LENGTH: 84
<212> TYPE: DNA

```
<213> ORGANISM: Artificial Sequence
<220> FEATURE:
<223> OTHER INFORMATION: 150_4G1C_3Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (69)..(69)
<223> OTHER INFORMATION: 2'-O-methylRNA
<220> FEATURE:
<221> NAME/KEY: modified_base
<222> LOCATION: (73)..(73)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (81)..(81)
<223> OTHER INFORMATION: 2'-O-methylRNA

<400> SEQUENCE: 6
tttttttttt cttttttttt tcttttttttt ttcttttttt tttctttttt ttttcttttc      60
ggggcactgg tacaagggtt ggga                                              84

<210> SEQ ID NO 7
<211> LENGTH: 84
<212> TYPE: DNA
<213> ORGANISM: Artificial Sequence
<220> FEATURE:
<223> OTHER INFORMATION: 150_4G1C_4Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (70)..(70)
<223> OTHER INFORMATION: 2'-O-methylRNA
<220> FEATURE:
<221> NAME/KEY: modified_base
<222> LOCATION: (75)..(75)
<223> OTHER INFORMATION: 2'-O-methylRNA
<220> FEATURE:
<221> NAME/KEY: modified_base
<222> LOCATION: (80)..(80)
<223> OTHER INFORMATION: 2'-O-methylRNA

<400> SEQUENCE: 7
tttttttttt cttttttttt tcttttttttt ttcttttttt tttctttttt ttttcttttc      60
ggggcactgg tacaagggtu ggga                                              84

<210> SEQ ID NO 8
<211> LENGTH: 84
<212> TYPE: DNA
<213> ORGANISM: Artificial Sequence
<220> FEATURE:
<223> OTHER INFORMATION: 150_4G1C_5Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
```

```
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA

<400> SEQUENCE: 8
tttttttttt cttttttttt tcttttttttt ttcttttttt tttcttttttt ttttcttttc    60 ggggcactgg uacaagggtt ggga                                            84

<210> SEQ ID NO 9
<211> LENGTH: 85
<212> TYPE: DNA
<213> ORGANISM: Artificial Sequence
<220> FEATURE:
<223> OTHER INFORMATION: 192_6T
<220> FEATURE:
<221> NAME/KEY: misc_feature
<223> OTHER INFORMATION: cholesterol TEG at the 3' end

<400> SEQUENCE: 9
tttttttttt cttttttttt tcttttttttt ttcttttttt tttcttttttt ttttctttttt    60 ttttggctgt caattcatag gtcag                                           85

<210> SEQ ID NO 10
<211> LENGTH: 22
<212> TYPE: RNA
<213> ORGANISM: Artificial Sequence
<220> FEATURE:
<223> OTHER INFORMATION: miR-150/hsa-miR-150

<400> SEQUENCE: 10
ucucccaacc cuuguaccag ug                                              22

<210> SEQ ID NO 11
<211> LENGTH: 21
<212> TYPE: RNA
<213> ORGANISM: Artificial Sequence
<220> FEATURE:
<223> OTHER INFORMATION: miR-192 /hsa-miR-192

<400> SEQUENCE: 11
cugaccuaug aauugacagc c                                               21

<210> SEQ ID NO 12
<211> LENGTH: 88
<212> TYPE: DNA
<213> ORGANISM: Artificial Sequence
<220> FEATURE:
<223> OTHER INFORMATION: 182_3T_3G_1Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (67)..(67)
<223> OTHER INFORMATION: 2'-O-methylRNA
```

<220> FEATURE:
<221> NAME/KEY: modified_base
<222> LOCATION: (69)..(69)
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
<221> NAME/KEY: modified_base
<222> LOCATION: (73)..(73)
<223> OTHER INFORMATION: 2'-O-methylRNA
<220> FEATURE:
<221> NAME/KEY: modified_base
<222> LOCATION: (75)..(75)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (79)..(79)
<223> OTHER INFORMATION: 2'-O-methylRNA
<220> FEATURE:
<221> NAME/KEY: modified_base
<222> LOCATION: (81)..(81)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA
<220> FEATURE:
<221> NAME/KEY: modified_base
<222> LOCATION: (85)..(85)
<223> OTHER INFORMATION: 2'-O-methylRNA
<220> FEATURE:
<221> NAME/KEY: modified_base
<222> LOCATION: (87)..(87)
<223> OTHER INFORMATION: 2'-O-methylRNA

<400> SEQUENCE: 12 ttttttttt cttttttttt tcttttttt ttcttttttt tttcttttt ttttcttttt    60 tgggagugug agutctacca utgccaaa                                     88

<210> SEQ ID NO 13
<211> LENGTH: 88
<212> TYPE: DNA
<213> ORGANISM: Artificial Sequence
<220> FEATURE:
<223> OTHER INFORMATION: 182_3T_3G_2Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (68)..(68)
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
<221> NAME/KEY: modified_base
<222> LOCATION: (74)..(74)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base

```
<222> LOCATION: (80)..(80)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA
<220> FEATURE:
<221> NAME/KEY: modified_base
<222> LOCATION: (86)..(86)
<223> OTHER INFORMATION: 2'-O-methylRNA

<400> SEQUENCE: 13
tttttttttt ctttttttttt tctttttttt ttctttttttt tttctttttt ttttctttttt    60 tgggagtgtg agtuctacca ttgccaaa                                           88

<210> SEQ ID NO 14
<211> LENGTH: 88
<212> TYPE: DNA
<213> ORGANISM: Artificial Sequence
<220> FEATURE:
<223> OTHER INFORMATION: 182_3T_3G_3Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (69)..(69)
<223> OTHER INFORMATION: 2'-O-methylRNA
<220> FEATURE:
<221> NAME/KEY: modified_base
<222> LOCATION: (73)..(73)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (81)..(81)
<223> OTHER INFORMATION: 2'-O-methylRNA
<220> FEATURE:
<221> NAME/KEY: modified_base
<222> LOCATION: (85)..(85)
<223> OTHER INFORMATION: 2'-O-methylRNA

<400> SEQUENCE: 14
tttttttttt ctttttttttt tctttttttt ttctttttttt tttctttttt ttttctttttt    60 tgggagtgug agutctacca utgccaaa                                           88

<210> SEQ ID NO 15
<211> LENGTH: 88
<212> TYPE: DNA
<213> ORGANISM: Artificial Sequence
<220> FEATURE:
<223> OTHER INFORMATION: 182_3T_3G_4Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (70)..(70)
<223> OTHER INFORMATION: 2'-O-methylRNA
<220> FEATURE:
<221> NAME/KEY: modified_base
<222> LOCATION: (75)..(75)
```

```
<223> OTHER INFORMATION: 2'-O-methylRNA
<220> FEATURE:
<221> NAME/KEY: modified_base
<222> LOCATION: (80)..(80)
<223> OTHER INFORMATION: 2'-O-methylRNA
<220> FEATURE:
<221> NAME/KEY: modified_base
<222> LOCATION: (85)..(85)
<223> OTHER INFORMATION: 2'-O-methylRNA

<400> SEQUENCE: 15
tttttttttt cttttttttt tctttttttt ttctttttt tttctttttt tttctttttt    60
tgggagtgtg agttctacca ttgccaaa                                        88

<210> SEQ ID NO 16
<211> LENGTH: 88
<212> TYPE: DNA
<213> ORGANISM: Artificial Sequence
<220> FEATURE:
<223> OTHER INFORMATION: 182_3T_3G_5Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA

<400> SEQUENCE: 16
tttttttttt cttttttttt tctttttttt ttctttttt tttctttttt tttctttttt    60
tgggagtgtg agttctacca ttgccaaa                                        88

<210> SEQ ID NO 17
<211> LENGTH: 24
<212> TYPE: RNA
<213> ORGANISM: Artificial Sequence
<220> FEATURE:
<223> OTHER INFORMATION: miR-182/hsa-miR-182

<400> SEQUENCE: 17
uuuggcaaug guagaacuca cacu                                            24

<210> SEQ ID NO 18
<211> LENGTH: 61
<212> TYPE: DNA
<213> ORGANISM: Artificial Sequence
<220> FEATURE:
<223> OTHER INFORMATION: DNA sequence

<400> SEQUENCE: 18
tttttttttt cttttttttt tctttttttt ttctttttt tttctttttt tttctttttt    60
t                                                                     61

<210> SEQ ID NO 19
<211> LENGTH: 21
<212> TYPE: DNA
```

```
<213> ORGANISM: Artificial Sequence
<220> FEATURE:
<223> OTHER INFORMATION: DNA sequence

<400> SEQUENCE: 19
tcaatcacag atagcacccc t                                              21

<210> SEQ ID NO 20
<211> LENGTH: 21
<212> TYPE: DNA
<213> ORGANISM: Artificial Sequence
<220> FEATURE:
<223> OTHER INFORMATION: RNA sequence
<220> FEATURE:
<221> NAME/KEY: modified_base
<222> LOCATION: (1)..(21)
<223> OTHER INFORMATION: 2'-O-methylRNA

<400> SEQUENCE: 20
tcaatcacag atagcacccc t                                              21

<210> SEQ ID NO 21
<211> LENGTH: 21
<212> TYPE: RNA
<213> ORGANISM: Artificial Sequence
<220> FEATURE:
<223> OTHER INFORMATION: miR-342

<400> SEQUENCE: 21
aggggugcua ucugugauug a                                              21

<210> SEQ ID NO 22
<211> LENGTH: 88
<212> TYPE: DNA
<213> ORGANISM: Artificial Sequence
<220> FEATURE:
<223> OTHER INFORMATION: 182_6T_1Alt
<220> FEATURE:
<221> NAME/KEY: misc_feature
<223> OTHER INFORMATION: cholesterol TEG at the 3' end
<220> FEATURE:
<221> NAME/KEY: modified_base
<222> LOCATION: (65)..(65)
<223> OTHER INFORMATION: 2'-O-methylRNA
<220> FEATURE:
<221> NAME/KEY: modified_base
<222> LOCATION: (67)..(67)
<223> OTHER INFORMATION: 2'-O-methylRNA
<220> FEATURE:
<221> NAME/KEY: modified_base
<222> LOCATION: (69)..(69)
<223> OTHER INFORMATION: 2'-O-methylRNA
<220> FEATURE:
<221> NAME/KEY: modified_base
<222> LOCATION: (71)..(71)
<223> OTHER INFORMATION: 2'-O-methylRNA
<220> FEATURE:
<221> NAME/KEY: modified_base
<222> LOCATION: (73)..(73)
<223> OTHER INFORMATION: 2'-O-methylRNA
<220> FEATURE:
<221> NAME/KEY: modified_base
<222> LOCATION: (75)..(75)
<223> OTHER INFORMATION: 2'-O-methylRNA
<220> FEATURE:
<221> NAME/KEY: modified_base
<222> LOCATION: (77)..(77)
<223> OTHER INFORMATION: 2'-O-methylRNA
<220> FEATURE:
<221> NAME/KEY: modified_base
<222> LOCATION: (79)..(79)
<223> OTHER INFORMATION: 2'-O-methylRNA
<220> FEATURE:
```

```
<221> NAME/KEY: modified_base
<222> LOCATION: (81)..(81)
<223> OTHER INFORMATION: 2'-O-methylRNA
<220> FEATURE:
<221> NAME/KEY: modified_base
<222> LOCATION: (83)..(83)
<223> OTHER INFORMATION: 2'-O-methylRNA
<220> FEATURE:
<221> NAME/KEY: modified_base
<222> LOCATION: (85)..(85)
<223> OTHER INFORMATION: 2'-O-methylRNA
<220> FEATURE:
<221> NAME/KEY: modified_base
<222> LOCATION: (87)..(87)
<223> OTHER INFORMATION: 2'-O-methylRNA

<400> SEQUENCE: 22
tttttttttt cttttttttt tctttttttt ttcttttttt tttcttttttt ttttcttttt    60 ttttagugug agutctacca utgccaaa                                        88

<210> SEQ ID NO 23
<211> LENGTH: 21
<212> TYPE: DNA
<213> ORGANISM: Artificial Sequence
<220> FEATURE:
<223> OTHER INFORMATION: DNA sequence

<400> SEQUENCE: 23
ggctgtcaat tcataggtca g                                                21

<210> SEQ ID NO 24
<211> LENGTH: 22
<212> TYPE: DNA
<213> ORGANISM: Artificial Sequence
<220> FEATURE:
<223> OTHER INFORMATION: DNA sequence

<400> SEQUENCE: 24
ctcggggcag ctcagtacag ga                                               22

<210> SEQ ID NO 25
<211> LENGTH: 23
<212> TYPE: RNA
<213> ORGANISM: Artificial Sequence
<220> FEATURE:
<223> OTHER INFORMATION: hsa-miR-342

<400> SEQUENCE: 25 aaagggugc uaucugugau uga                                               23

<210> SEQ ID NO 26
<211> LENGTH: 22
<212> TYPE: RNA
<213> ORGANISM: Artificial Sequence
<220> FEATURE:
<223> OTHER INFORMATION: hsa-miR-486

<400> SEQUENCE: 26
uccuguacug agcugccccg ag                                               22

<210> SEQ ID NO 27
<211> LENGTH: 20
<212> TYPE: DNA
<213> ORGANISM: Artificial Sequence
<220> FEATURE:
<223> OTHER INFORMATION: nucleotide sequence in Fig 1
<220> FEATURE:
<221> NAME/KEY: misc_RNA
```

<222> LOCATION: (7)..(7)
<223> OTHER INFORMATION: RNA

<400> SEQUENCE: 27
cactgguaca agggttggga                                                    20

<210> SEQ ID NO 28
<211> LENGTH: 20
<212> TYPE: DNA
<213> ORGANISM: Artificial Sequence
<220> FEATURE:
<223> OTHER INFORMATION: nucleotide sequence in Fig 1
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (7)..(7)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (19)..(19)
<223> OTHER INFORMATION: 2'-O-methylRNA

<400> SEQUENCE: 28
cactgguaca agggttggga                                                    20

<210> SEQ ID NO 29
<211> LENGTH: 20
<212> TYPE: DNA
<213> ORGANISM: Artificial Sequence
<220> FEATURE:
<223> OTHER INFORMATION: nucleotide sequence in Fig 1
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (6)..(6)
<223> OTHER INFORMATION: 2'-O-methylRNA
<220> FEATURE:
<221> NAME/KEY: modified_base
<222> LOCATION: (11)..(11)
<223> OTHER INFORMATION: 2'-O-methylRNA
<220> FEATURE:
<221> NAME/KEY: modified_base
<222> LOCATION: (16)..(16)
<223> OTHER INFORMATION: 2'-O-methylRNA

<400> SEQUENCE: 29
cactggtaca agggtuggga                                                    20

<210> SEQ ID NO 30
<211> LENGTH: 20
<212> TYPE: DNA
<213> ORGANISM: Artificial Sequence
<220> FEATURE:
<223> OTHER INFORMATION: nucleotide sequence in Fig 1
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (5)..(5)
<223> OTHER INFORMATION: 2'-O-methylRNA
<220> FEATURE:

```
<221> NAME/KEY: modified_base
<222> LOCATION: (9)..(9)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (17)..(17)
<223> OTHER INFORMATION: 2'-O-methylRNA

<400> SEQUENCE: 30
cactggtaca agggttggga                                                     20

<210> SEQ ID NO 31
<211> LENGTH: 20
<212> TYPE: DNA
<213> ORGANISM: Artificial Sequence
<220> FEATURE:
<223> OTHER INFORMATION: nucleotide sequence in Fig 1
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (4)..(4)
<223> OTHER INFORMATION: 2'-O-methylRNA
<220> FEATURE:
<221> NAME/KEY: modified_base
<222> LOCATION: (7)..(7)
<223> OTHER INFORMATION: 2'-O-methylRNA
<220> FEATURE:
<221> NAME/KEY: modified_base
<222> LOCATION: (10)..(10)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (16)..(16)
<223> OTHER INFORMATION: 2'-O-methylRNA
<220> FEATURE:
<221> NAME/KEY: modified_base
<222> LOCATION: (19)..(19)
<223> OTHER INFORMATION: 2'-O-methylRNA

<400> SEQUENCE: 31
cacugguaca agggtuggga                                                     20

<210> SEQ ID NO 32
<211> LENGTH: 20
<212> TYPE: DNA
<213> ORGANISM: Artificial Sequence
<220> FEATURE:
<223> OTHER INFORMATION: nucleotide sequence in Fig 1
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (3)..(3)
<223> OTHER INFORMATION: 2'-O-methylRNA
<220> FEATURE:
<221> NAME/KEY: modified_base
<222> LOCATION: (5)..(5)
<223> OTHER INFORMATION: 2'-O-methylRNA
<220> FEATURE:
<221> NAME/KEY: modified_base
<222> LOCATION: (7)..(7)
<223> OTHER INFORMATION: 2'-O-methylRNA
```

<220> FEATURE:
<221> NAME/KEY: modified_base
<222> LOCATION: (9)..(9)
<223> OTHER INFORMATION: 2'-O-methylRNA
<220> FEATURE:
<221> NAME/KEY: modified_base
<222> LOCATION: (11)..(11)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (15)..(15)
<223> OTHER INFORMATION: 2'-O-methylRNA
<220> FEATURE:
<221> NAME/KEY: modified_base
<222> LOCATION: (17)..(17)
<223> OTHER INFORMATION: 2'-O-methylRNA
<220> FEATURE:
<221> NAME/KEY: modified_base
<222> LOCATION: (19)..(19)
<223> OTHER INFORMATION: 2'-O-methylRNA

<400> SEQUENCE: 32
cactgguaca agggutggga                                          20

<210> SEQ ID NO 33
<211> LENGTH: 24
<212> TYPE: DNA
<213> ORGANISM: Artificial Sequence
<220> FEATURE:
<223> OTHER INFORMATION: nucleotide sequence in Fig 2
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (7)..(7)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (19)..(19)
<223> OTHER INFORMATION: 2'-O-methylRNA

<400> SEQUENCE: 33
agtgtgagtt ctaccattgc caaa                                     24

<210> SEQ ID NO 34
<211> LENGTH: 24
<212> TYPE: DNA
<213> ORGANISM: Artificial Sequence
<220> FEATURE:
<223> OTHER INFORMATION: nucleotide sequence in Fig 2
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (6)..(6)
<223> OTHER INFORMATION: 2'-O-methylRNA
<220> FEATURE:
<221> NAME/KEY: modified_base
<222> LOCATION: (11)..(11)
<223> OTHER INFORMATION: 2'-O-methylRNA
<220> FEATURE:
<221> NAME/KEY: modified_base
<222> LOCATION: (16)..(16)

```
<223> OTHER INFORMATION: 2'-O-methylRNA
<220> FEATURE:
<221> NAME/KEY: modified_base
<222> LOCATION: (21)..(21)
<223> OTHER INFORMATION: 2'-O-methylRNA

<400> SEQUENCE: 34
agtgtgagtt ctaccattgc caaa                                              24

<210> SEQ ID NO 35
<211> LENGTH: 24
<212> TYPE: DNA
<213> ORGANISM: Artificial Sequence
<220> FEATURE:
<223> OTHER INFORMATION: nucleotide sequence in Fig 2
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (5)..(5)
<223> OTHER INFORMATION: 2'-O-methylRNA
<220> FEATURE:
<221> NAME/KEY: modified_base
<222> LOCATION: (9)..(9)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (17)..(17)
<223> OTHER INFORMATION: 2'-O-methylRNA
<220> FEATURE:
<221> NAME/KEY: modified_base
<222> LOCATION: (21)..(21)
<223> OTHER INFORMATION: 2'-O-methylRNA

<400> SEQUENCE: 35
agtgugagut ctaccautgc caaa                                              24

<210> SEQ ID NO 36
<211> LENGTH: 24
<212> TYPE: DNA
<213> ORGANISM: Artificial Sequence
<220> FEATURE:
<223> OTHER INFORMATION: nucleotide sequence in Fig 2
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (4)..(4)
<223> OTHER INFORMATION: 2'-O-methylRNA
<220> FEATURE:
<221> NAME/KEY: modified_base
<222> LOCATION: (7)..(7)
<223> OTHER INFORMATION: 2'-O-methylRNA
<220> FEATURE:
<221> NAME/KEY: modified_base
<222> LOCATION: (10)..(10)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (16)..(16)
<223> OTHER INFORMATION: 2'-O-methylRNA
<220> FEATURE:
<221> NAME/KEY: modified_base
```

<222> LOCATION: (19)..(19)
<223> OTHER INFORMATION: 2'-O-methylRNA
<220> FEATURE:
<221> NAME/KEY: modified_base
<222> LOCATION: (22)..(22)
<223> OTHER INFORMATION: 2'-O-methylRNA

<400> SEQUENCE: 36
agtgtgagtu ctaccattgc caaa                                              24

<210> SEQ ID NO 37
<211> LENGTH: 24
<212> TYPE: DNA
<213> ORGANISM: Artificial Sequence
<220> FEATURE:
<223> OTHER INFORMATION: nucleotide sequence in Fig 2
<220> FEATURE:
<221> NAME/KEY: modified_base
<222> LOCATION: (1)..(1)
<223> OTHER INFORMATION: 2'-O-methylRNA
<220> FEATURE:
<221> NAME/KEY: modified_base
<222> LOCATION: (3)..(3)
<223> OTHER INFORMATION: 2'-O-methylRNA
<220> FEATURE:
<221> NAME/KEY: modified_base
<222> LOCATION: (5)..(5)
<223> OTHER INFORMATION: 2'-O-methylRNA
<220> FEATURE:
<221> NAME/KEY: modified_base
<222> LOCATION: (7)..(7)
<223> OTHER INFORMATION: 2'-O-methylRNA
<220> FEATURE:
<221> NAME/KEY: modified_base
<222> LOCATION: (9)..(9)
<223> OTHER INFORMATION: 2'-O-methylRNA
<220> FEATURE:
<221> NAME/KEY: modified_base
<222> LOCATION: (11)..(11)
<223> OTHER INFORMATION: 2'-O-methylRNA
<220> FEATURE:
<221> NAME/KEY: modified_base
<222> LOCATION: (13)..(13)
<223> OTHER INFORMATION: 2'-O-methylRNA
<220> FEATURE:
<221> NAME/KEY: modified_base
<222> LOCATION: (15)..(15)
<223> OTHER INFORMATION: 2'-O-methylRNA
<220> FEATURE:
<221> NAME/KEY: modified_base
<222> LOCATION: (17)..(17)
<223> OTHER INFORMATION: 2'-O-methylRNA
<220> FEATURE:
<221> NAME/KEY: modified_base
<222> LOCATION: (19)..(19)
<223> OTHER INFORMATION: 2'-O-methylRNA
<220> FEATURE:
<221> NAME/KEY: modified_base
<222> LOCATION: (21)..(21)
<223> OTHER INFORMATION: 2'-O-methylRNA
<220> FEATURE:
<221> NAME/KEY: modified_base
<222> LOCATION: (23)..(23)
<223> OTHER INFORMATION: 2'-O-methylRNA

<400> SEQUENCE: 37
agugugagut ctaccautgc caaa                                              24

METHOD

RELATED APPLICATIONS

This Application is a national stage filing under 35 U.S.C. 371 of international application number PCT/GB2017/053177, filed Oct. 20, 2017, which claims the benefit of United Kingdom application number 1617886.5, filed Oct. 21, 2016, each of which is herein incorporated by reference in its entirety.

FIELD OF THE INVENTION

The invention relates to methods of determining in a sample the presence, absence or amount of target polynucleotides. The invention also relates to a panel of probes for use in the methods and to kits for carrying out the methods.

BACKGROUND OF THE INVENTION

Transmembrane pores (nanopores) have great potential as direct, electrical biosensors for a variety of analytes, such as polymers and small molecules. When a potential is applied across a nanopore, there is a change in the current flow when a molecule, such as a polynucleotide, resides transiently in the barrel or channel of the nanopore for a certain period of time. Specific molecules, such as specific polynucleotides, give current changes of known signature and duration. Such current changes can be used to identify the polynucleotide present in the pore.

A transmembrane pore can be used in a multiplex assay to determine the presence or absence of each analyte in a group of two or more analytes. The multiplex assay uses a panel of probes. Each probe in the panel includes a tail that is capable of entering the pore and affecting the current flowing through the pore and an analyte-binding region. Each tail affects the current flowing through the pore in a different and distinctive way depending on whether or not the probe is bound to one of the analytes of interest. The effect each probe in the panel has on the current flowing through the pore is also distinctive so that the identity of each probe can be detected.

SUMMARY OF THE INVENTION

The inventors have developed an assay for determining the presence, absence or concentration/amount of one or more target polynucleotides using a transmembrane pore. The assay utilises a panel of probes, each comprising a region capable of hybridising to a target polynucleotide and a non-hybridisation region (tail). When the probe is hybridised to its target polynucleotide, and brought into contact with a transmembrane pore across which a electric field is applied, the non-hybridisation region will enter the transmembrane pore and be held there until the target polynucleotide dehybridises from the probe. The dwell time may be defined as the length of a current blockade, wherein the current blockade is the reduction in ion current flow through the pore due to the presence of a component in the sample that interacts with the pore.

The length of the current blockade may be defined as the period of time between when a component in the sample gives rise to a reduction in the ion current until such time when the component no longer gives rise to a reduction in said current. For a given pore and potential, the dwell time is dependent upon the time it takes for the target polynucleotide to de-hybridise from the probe under the force of an applied potential. The strength of the applied potential and the dimensions of the pore also affect dwell time.

The inventors have recognised that a panel of probes can be constructed to provide approximately the same dwell time and can be used in a transmembrane pore-based assay to determine the presence, absence or amount of a target polynucleotide. This is particularly advantageous, for example, when the sample comprising the target polynucleotides contains other components that interact with the transmembrane pore. Only current blockades of certain dwell times need to be analysed in the method. Longer and/or shorter current blockades can be excluded from the analysis. The inventors have found that a panel of probes having approximately the same dwell times may be designed by adjusting the composition of the hybridisation region of one or more probes in the panel. The inventors have found that the length of time a probe remains hybridised to its target polynucleotide can be increased or decreased by introducing non-natural nucleotides into the hybridisation region.

Accordingly, in one aspect the invention provides a method for determining the presence, absence or amount of two or more target polynucleotides in a sample comprising additional components, the method comprising:

(i) contacting the sample with a panel of two or more probes under conditions suitable for hybridisation of the target polynucleotides to the probes, wherein:
  (a) each probe comprises a non-hybridisation region and a hybridisation region that specifically hybridises to one of the target polynucleotides to form a hybridised probe; and
  (b) the hybridisation region of a probe of the panel comprises one or more non-natural nucleotides;

(ii) contacting the sample prepared in step (i) with a transmembrane pore through which a single stranded polynucleotide but not a double stranded polynucleotide can pass and applying a potential difference to the transmembrane pore such that the hybridised probes in the sample interact with the pore;

(iii) measuring current blockades having a duration within a defined window, wherein:
  (a) the one or more non-natural nucleotides present in the hybridisation region of the probe increase or decrease the duration of the current blockade due to the probe hybridised to its target polynucleotide such that the proportion of current blockades that occur within the window due to the interaction of the hybridised probes with the pore is increased compared to when the corresponding one or more natural nucleotides are present in the hybridisation region; and
  (b) each hybridised probe gives rise to a current blockade indicative of that probe; and (iv) correlating the measured current blockades with the probes, thereby determining the presence, absence or amount of the two or more target polynucleotides in the sample.

Further aspects of the invention include:
  a method of diagnosing a disease, wherein the method comprises carrying out the described method for determining the presence, absence or amount of two or more target polynucleotides, wherein the target polynucleotides are markers of the disease;
  a panel of two or more probes for use in a method for determining the presence, absence or amount of two or more target polynucleotides; and use of a panel of probes of the invention in a method of detecting the presence, absence or amount of two or more target polynucleotides.

DESCRIPTION OF THE FIGURES

It is to be understood that Figures are for the purpose of illustrating particular embodiments of the invention only, and are not intended to be limiting.

DESCRIPTION OF THE SEQUENCE LISTING

Figure 1:
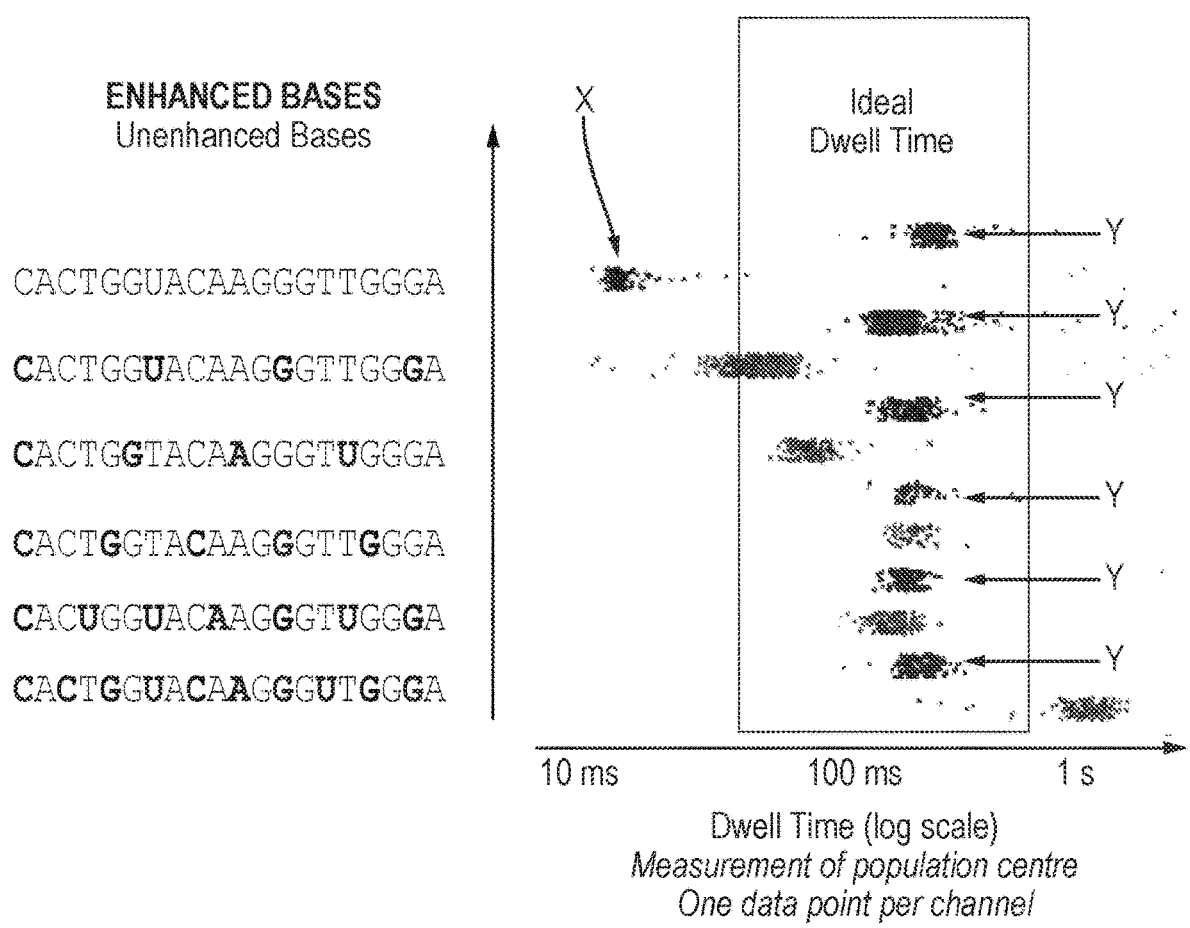
FIG. 1 shows mean current blockade lengths for the calibration duplex (formed with MicroRNA 192, and labelled Y) and each microRNA 150 variant and duplexes (SEQ ID NOs: 27-32).

SEQ ID NO: 1 is an example of a quadruplex-forming sequence.

SEQ ID NO: 2 is the polynucleotide sequence encoding one monomer of α-hemolysin-E111N/K147N ((α-HL-NN; Stoddart et al., PNAS, 2009; 106(19): 7702-7707).

SEQ ID NO: 3 is the amino acid sequence of one monomer of α-HL-NN.

SEQ ID Nos: 4 to 26 show polynucleotide sequences which are used in the Examples.

It is to be understood that sequences are not intended to be limiting.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a tail" includes two or more such tails, reference to "a polynucleotide" includes two or more such polynucleotides, and the like.

All publications, patents and patent applications cited herein, whether supra or infra, are hereby incorporated by reference in their entirety.

Methods

The inventors have developed an assay for detecting and/or analyzing one or more target polynucleotides, e.g., determining the presence, absence, or concentration/amount of one or more target polynucleotides using a transmembrane pore. In one aspect, provided herein relates to an assay that utilizes a panel of probes, each comprising a region capable of hybridising to a target polynucleotide (e.g., a hybridization region) and a non-hybridisation region. Upon the hybridization between the hybridization region of the probe and a portion of a target polynucleotide, a potential is applied across a transmembrane pore to cause at least a portion of the non-hybridisation region of the probe to enter the transmembrane pore and interact with the transmembrane pore, thus reducing ion current flow through the transmembrane pore. The portion of the non-hybridization region that interacts with the pore remains within the transmembrane pore until the target polynucleotide dehybridises from the hybridization region of the probe. Dehybridisation is caused by the unzipping effect of the pore (i.e., the applied voltage across the membrane). Measurement is taken when target and probe are hybridised but ultimately the target will fully dehybridise from the hybridisation region of the probe. The length of time during which the portion of the non-hybridization region that interacts with the transmembrane pore remains within the transmembrane pore generally corresponds to the length of time during which a current blockade occurs. This is referred to as "dwell time." Thus, the dwell time may be defined as the length of time during which a current blockade occurs, wherein the current blockade is indicative of a reduction in ion current flow through the pore due to the presence of a component in a sample that interacts with the pore. The length of time during which a current blockade occurs may be defined as the period of time between when a component in a sample gives rise to a reduction in the ion current flow through the transmembrane pore and when the component no longer does so. For a given transmembrane pore and potential, the dwell time can depend upon the time it takes for the target polynucleotide to de-hybridise from the hybridization region of the probe under the force of an applied potential. In some embodiments, the strength of an applied potential and/or the dimensions of the pore can also affect dwell time. In some embodiments, the binding affinity between the hybridization region of the probe and the corresponding portion of the target polynucleotide may also affect dwell time.

The inventors have recognised that a panel of probes constructed to provide approximately the same dwell time (e.g., within 10% difference, within 5% difference, or within 1% difference) can be used in a transmembrane pore-based assay to determine the presence, absence, or amount of one or more target polynucleotides. The dwell time window typically ranges from 1 nanosecond to 100 seconds, 10 microseconds to 10 seconds. A dwell time window of about 0.5 seconds is optimal.

For example, this is particularly advantageous when a sample comprising target polynucleotides contains other components (e.g., non-target polynucleotides and/or non-target analytes) that can interact with the transmembrane pore. Only current blockades of certain dwell times need to be analysed to determine the presence, absence, or amount of target polynucleotide(s). Longer and/or shorter current blockades can be excluded from the analysis.

A panel of probes having approximately the same dwell time window may be designed by varying the composition or make-up of the hybridisation region of one or more probes in the panel. The inventors have found that the length of time for which the hybridization region of a probe remains hybridised to the corresponding portion of a target polynucleotide can be increased or decreased by introducing appropriate types, patterns, and/or numbers of non-natural nucleotides into the hybridisation region.

The inventors have also shown that the panel of probes can be designed to perform a multiplex polynucleotide assay (e.g., to distinguish a first target polynucleotide from a second target polynucleotide). For example, by designing the non-hybridization region of each probe in the panel to confer a unique signal pattern that is indicative of a distinct target polynucleotide, which is combined with the feature of the probes having approximately the same dwell time window as discussed above, current blockade signal patterns that occur with a defined dwell time window can be analyzed to detect a plurality of (e.g., 2, 3, 4, 5, 6, 7, 8, 9, 10, or more) distinct target polynucleotides in a sample. In addition to the probes having approximately the same dwell time window, the non-hybridization region of each probe should be constructed to confer a unique signal pattern that is indicative of a distinct target polynucleotide, in order to permit a multiplexing assay. In one embodiment, the non-hybridisation region of each probe may comprise poly T's or abasic nucleotides. Abasic nucleotides have neither a purine nor a pyrimidine base.

In one aspect, the invention provides a method of determining the presence or absence or amount of two or more target polynucleotides in a sample comprising additional components.

The method comprises contacting a sample with a panel of two or more probes. This step is carried out under conditions suitable for hybridisation of the target polynucleotides to the probes. Each probe in the panel binds specifically to a target polynucleotide and comprises a non-hybridisation region and a hybridisation region. The hybridisation region specifically hybridises to a target polynucleotide. The non-hybridisation region is capable of entering a transmembrane pore through which a single stranded polynucleotide but not a double stranded polynucleotide can pass under an applied potential difference. The non-hybridisation region has different effects on the current flowing through the pore depending on whether or not the probe is hybridised to its target polynucleotide.

The probes are typically contacted with the sample under conditions which permit the probes to hybridise to their respective target polynucleotides, if the target polynucleotides are present in the sample. Conditions that permit hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na+) SSC at 60° C.

Suitable conditions for hybridisation include 40 mM KCl, 10 mM HEPES, pH 8, at about 97° C. for 2.5 minutes. The temperature is then decreased by 0.1° C. every 5 seconds until the temperature reaches 20° C. Preferred hybridisation conditions are those described in the Examples. In a particular example, the hybridisation conditions are 50 mM NaCl, 10 mM Tris pH7.5 at about 95° C. for 2.5 minutes. The temperature is then reduced by 0.1° C. every 5 seconds until the temperature reaches about 18° C. After hybridisation, the probe may be kept at about 4° C. prior to analysis.

The method comprises contacting the sample with a transmembrane pore through which a single stranded polynucleotide but not a double stranded polynucleotide can pass. When the sample and panel of probes are brought into contact with a transmembrane pore, a potential is preferably applied across the pore. This allows the hybridised probes in the sample to interact with the pore. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11:129(27):8650-5.

Typically the hybridisation region will be at least about 80%, such as at least about 85% at least about 90%, at least about 95%, at least about 97% or at least 100% complementary to a sequence within the target polynucleotide.

The method also comprises measuring the ion current flow through the pore to determine which probes in the panel, if any, have bound to a target polynucleotide and thereby determining the presence or absence, and optionally the concentration/amount, of one or more target polynucleotides in the sample. The measurement of ion current flow may comprise measuring a current or measuring an optical signal indicative of the flow. The current may be measured using any method known in the art. Different probes in the panel affect the current flowing through the pore in different and distinctive manners when hybridised to their respective target polynucleotides. This allows a particular probe in the panel to be identified. Since both the identity of a probe and its binding to a target polynucleotide can be measured, the presence or absence, and optionally the amount, of the target polynucleotide in the sample can be determined. The method therefore comprises correlating the measured current blockades with the probes, thereby determining the presence or absence, and optionally the amount, of the two or more target polynucleotides in the sample.

The hybridisation region of at least one probe of the panel comprises one or more non-natural nucleotides. The one or more non-natural nucleotides present in the hybridisation region of the probe increase or decrease the duration of the current blockade due to the probe hybridised to its target polynucleotide such that the proportion of current blockades that occur within a defined window that are due to the interaction of the hybridised probes with the pore is increased compared to when the corresponding one or more natural nucleotides are present in the hybridisation region. The duration of the current blockade obtained using a hybridisation sequence that contains the non-natural nucleotide may, for example, be increased or decreased by about 50%, about 20%, about 10% about 5% or about 1% compared to the duration of the current blockade obtaining using a hybridisation sequence that does not contain the non-natural nucleotide. This allows the presence or absence of the target polynucleotides to be determined by measuring only current blockades that fall within a defined window. Current blockades caused by components in the sample other than the hybridised pores can be excluded from the analysis. The additional components may, for example, comprise one or more of non-target polynucleotides, folded and unfolded proteins, peptides, carbohydrates, short polymers and cell debris. The method of the invention is therefore particularly useful in the analysis of dirty samples or samples of complex matrices, such as biological samples, and/or samples containing low concentrations of one or more of the target polynucleotides. A low concentration could be for example a concentration measured in femtomoles, attomoles, micromoles or nanomoles.

The output from the assay may be analysed in real time, allowing the assay to be stopped when sufficient information has been obtained. The method allows the detection of multiple polynucleotides in a single sample with minimal, or no, sample preparation, for example a sample of bodily fluid taken directly from a patient, thus allowing the method to be carried out by someone with minimal training or qualification. This removes or reduces the need to involve washing steps or steps to remove unbound probes and/or polynucleotides in the sample preparation.

Sample

The sample may be any suitable sample. A suitable sample is a sample amenable to the methods described herein. The method is typically carried out on a sample that is known to contain or suspected of containing at least one, such as at least two or more, of the target polynucleotides. The method allows target polynucleotides to be detected in the presence of other components in a sample. The method filters the current blockades resulting from probes interacting with their target polypeptides from current blockades resulting from other components present in the sample. Such other components include but are not limited to, for example, one or more of the following: proteins, which may be folded or unfolded, peptides, carbohydrates, polymers, such as non-target polynucleotides, and cell debris.

The sample may be a biological sample. The method may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus.

The sample may be a fluid sample. In one embodiment, the sample may comprise a body fluid. The body fluid may be obtained from a human or animal. The human or animal may have, be suspected of having or be at risk of a disease. The sample may be urine, lymph, saliva, mucus, seminal fluid or amniotic fluid, but is preferably whole blood, plasma or serum. Typically, the sample is human in origin, but alternatively it may be from another mammal such as from commercially farmed animals such as horses, cattle, sheep or pigs or may alternatively be pets such as cats or dogs. The sample may be a cell suspension or tissue homogenate.

Alternatively, a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea or coffee.

The sample may be a non-biological sample. The non-biological sample is preferably a fluid sample. Examples of non-biological samples include surgical fluids, water such as drinking water, sea water or river water, and reagents for laboratory tests.

The sample may be processed prior to being assayed, for example by centrifugation or by passage through a membrane that filters out unwanted molecules or cells, such as red blood cells. The sample may be measured immediately upon being taken. The sample may also be typically stored prior to assay, for example at a temperature of $-70°$ C., or below $-70°$ C.

Target Polynucleotides

The panel of probes or probe can be used to determine the presence, absence or amount of one or more target polynucleotides, such as 1, 2, 5, 10, 15, 20, 30, 40, 50, 100, 500, 1000, 1500, 1750, 2000 or more target polynucleotides. Preferably the panel of probes or probe can be used to determine the presence, absence or amount of from about 1 to about 2000 polynucleotides, such as from about 5 to about 1500 polynucleotides, from about 10 to about 1000 polynucleotides, from about 20 to about 500 polynucleotides or from about 50 to about 100 polynucleotides.

A polynucleotide is a macromolecule comprising two or more nucleotides. The target polynucleotide may comprise any combination of any nucleotides. The nucleotides can be naturally occurring or artificial. One or more nucleotides in the target polynucleotide can be oxidised or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag.

The target polynucleotides may be single stranded or double stranded. At least a portion of the polynucleotide may be double stranded. The target polynucleotide is preferably single stranded. The target polynucleotide may be one strand from a double stranded polynucleotide. The polynucleotides can be nucleic acids, such as deoxyribonucleic acid (DNA) or ribonucleic acid (RNA). The polynucleotides can comprise one strand of RNA hybridised to one strand of DNA. The polynucleotides may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotides may comprise any of the nucleotides discussed herein, including the abasic and modified nucleotides.

The target polynucleotide can be a polynucleotide that is secreted from cells. Alternatively, the target polynucleotide can be a polynucleotide that is present inside cells such that the polynucleotide must be extracted from the cells before the invention can be carried out.

The target polynucleotides can be any length. For example, the polynucleotides can be at least 7, least 10, at least 50, at least 100, at least 150, at least 200, at least 250, at least 300, at least 400 or at least 500 nucleotides or nucleotide pairs in length. For example, the polynucleotides may be from about 7 to about 200 nucleotides, about 10 to about 500 nucleotide, about 50 to about 400 nucleotides, about 100 to about 300 nucleotides or about 150 to about 250 nucleotides in length. The polynucleotides can be up to about 1000 or more nucleotides, up to about 5000 or more nucleotides in length or up to about 100000 or more nucleotides in length. The target polynucleotide may be an oligonucleotide. Oligonucleotides are short nucleotide polymers which typically have 50 or fewer nucleotides, such 40 or fewer, 30 or fewer, 20 or fewer, 10 or fewer or 5 or fewer nucleotides. The target oligonucleotide is preferably from about 15 to about 30 nucleotides in length, such as from about 20 to about 25 nucleotides in length. For example, the oligonucleotide can be about 15, about 16, about 17, about 18, about 19, about 20, about 21, about 22, about 23, about 24, about 25, about 26, about 27, about 28, about 29 or about 30 nucleotides in length.

The target polynucleotides may be any group of polynucleotides. For instance, the group may be associated with a particular phenotype. The group may be associated with a particular type of cell. For instance, the group may be indicative of a bacterial cell. The group may be indicative of a virus, a fungus or a parasite.

The target polynucleotides may be a group of two or more polynucleotides that are biomarkers associated with a particular disease or condition. The biomarkers can be used to diagnose or prognose the disease or condition. Suitable panels of biomarkers are known in the art, for example as described in Edwards et al. (2008) *Mol. Cell*. Proteomics 7, p 1824-1837; Jacquet et al. (2009), *Mol. Cell*. Proteomics 8, p 2687-2699; Anderson et al (2010) *Clin. Chem.* 56, 177-185. The disease or condition is preferably cancer, heart disease, including coronary heart disease and cardiovascular disease, or an infectious disease, such as sepsis. The target oligonucleotide or polynucleotide is preferably a microRNA (or miRNA) or siRNA. siRNAs are a class of double-stranded RNA molecules, 20-25 base pairs in length, similar to miRNA. The group of two or more target oligonucleotides or polynucleotides is preferably a group of two or more miRNAs. Suitable miRNAs for use in the invention are well known in the art. For instance, suitable miRNAs are stored on publically available databases (Jiang et al., (2009) "miR2Disease: a manually curated database for microRNA deregulation in human disease" Nucleic Acids Res. 37(database issue): D98-104).

Panel of Probes

The method comprises contacting a sample with a panel of two or more probes. In one aspect, the invention also provides a panel of two or more probes. The panel of two or more probes may be for determining in a sample the presence, absence or amount of one or more target polynucleotides. The two or more probes each comprise a non-hybridisation region and a hybridisation region, as described below. Each probe in the panel may further comprises an anchor that allows it to be coupled to a membrane. An exemplary anchor is a lipid binding molecule, such as cholesterol.

In the panel of probes, the non-hybridisation regions of at least two of the probes, such as at least three, at least four, at least five or more of the probes, in the panel are different from each other. In a method of determining the presence, absence or amount of at least two target polynucleotides that utilises such a panel of probes, the target polynucleotides hybridise with each one of the at least two probes. In one embodiment, each probe (i.e. each type of probe) in the panel comprises a unique non-hybridisation region. The differences between the different non-hybridisation regions in the probes in the panel may contribute to the distinctiveness of the effects each probe has on the current flowing through the pore.

The panel of probes typically comprises multiple copies of each or every probe in the panel. If a target polynucleotide is present in the sample, there will almost certainly be multiple instances of the target polynucleotide in the sample.

Preferably, each of the hybridisation regions in each of the probes is unique so that, when multiple copies of a target polynucleotide are present in a sample, the target polynucleotide hybridises only to one type of probe in the sample. In other words, it is preferred that no two probes (i.e. no two types of probe) in the panel comprise the same hybridisation region. This means that when a target polynucleotide is present in a sample it always gives rise to the same distinctive current blockade as largely determined by the non-hybridisation region of the probe to which it binds.

In one embodiment, two or more probes in the panel may comprise the same hybridisation region and different non-hybridisation regions. In this embodiment, the distinctiveness of the effects each probe has on the current flowing through pore is typically provided by the differences between the non-hybridisation regions. In this embodiment, two (or more) probes are targeted to the same target polynucleotide. This can provide an internal control because positive signals from both probes will be required to conclude that the target polynucleotide is present in the sample.

Two or more probes in the panel may comprise different hybridisation regions and the same non-hybridisation region. In this embodiment, the distinctiveness of the effects each probe has on the current flowing through pore is typically provided by the differences in the hybridisation regions. The hybridisation regions are designed so that they produce current blockades having similar durations. Therefore, any differences may be subtle. Therefore, this embodiment is of particular use where it is not desired to distinguish between the different target polynucleotides, or where the hybridisation regions bind to different parts of the same target polynucleotide.

In one embodiment, each probe (i.e. each type of probe) in the panel comprises a different hybridisation region and a different non-hybridisation region. In other words, each probe in the panel has a unique hybridisation region and a unique non-hybridisation region. In this embodiment, the hybridisation regions and different non-hybridisation regions typically both contribute to the distinctiveness of the effects each of the two or more probes has on the current flowing through pore. This facilitates distinguishing different target polynucleotides present in a sample.

The panel may comprise any number of two or more probes, such as 2, 5, 10, 15, 20, 30, 40, 50, 100 or more probes. The panel preferably has from about 4 to about 100 probes, such as from about 5 to about 80 probes, from about 10 to about 60 probes or from about 20 to about 50 probes. The number of probes (i.e. types of probes) in the panel is typically the same as or greater than number of target polynucleotides to be detected. If the number of probes in the panel is greater than the number of target polynucleotides, two or more probes may be targeted to the same target polynucleotide and the method of the invention comprises an internal control as discussed above.

The probe can be any length. For example, the probe may have a length of from about 17 to about 240 nucleotides. Such as from about 20 to about 200 nucleotides, about 30 to about 150, about 40 to about 100 or about 50 to about 70 nucleotides. The probe may be single stranded or may comprise one or more, such as two or three, single stranded portions and one or more, such as two or three, double stranded portions. The probe may comprise one or more linker between the hybridisation and non-hybridisation regions.

The hybridisation and non-hybridisation regions may be located anywhere in the probe. The non-hybridisation region may be 3' or 5' to the hybridisation region. Preferably, the non-hybridisation region is 5' to the hybridisation region in at least one, and preferably all, of the probes in the panel.

In one embodiment, at least one of the probes comprises a single hybridisation region and a single non-hybridisation region, e.g. the probe consists of, or consists essentially of, a single hybridisation region and a single non-hybridisation region. Typically all of the probes in the panel have the same basic structure, e.g. all contain the same number of hybridisation and non-hybridisation regions in the same orientation within the probe.

In some embodiments, at least one of the probes may further comprise a second non-hybridisation region in addition to the first non-hybridisation region and either a second hybridisation region, a quadruplex-forming sequence or a double-stranded region between the first and second non-hybridisation regions.

Preferably all of the probes in the panel have the same overall structure. For example, all of the probes may have the same arrangement of hybridisation and non-hybridisation regions and, where present, quadruplex-forming sequences and/or double stranded regions. In this embodiment the window of current blockades which are measured may encompass the current blockades resulting from the interaction of the whole probes with the pore. This is preferably the case where all of the probes have the same overall structure. Alternatively, the current blockades within the window that are measured may be partial current blockades, each corresponding to the time a non-hybridisation region of the probe interacts with the barrel or channel of the pore prior to dehybridisation of the hybridisation region adjacent to the non-hybridisation region in the pore. This is preferably the case where the probes have different overall structures, particularly where the probes have different numbers of hybridisation regions.

The two hybridisation regions may bind to the same target polynucleotide or to two different target polynucleotides. Where the two hybridisation regions bind to different target polynucleotides, the target polynucleotides are preferably associated in some way, for example are indicative of the same disease or condition.

Preferably, the two hybridisation regions both bind to the same target polynucleotide, and may be identical so that they bind to the same region of the target polynucleotide, or may bind to different parts of the same target polynucleotide. In either case, it is preferred that the non-hybridisation regions result in a current blockade within a predefined window.

Where the probe comprises a quadruplex-forming region or a double stranded region, the quadruplex or a double stranded region is incapable of passing through the pore, resulting in the second non-hybridisation region being held in the pore and enabling the current characteristic of the second non-hybridisation region to be measured. The time for which the second non-hybridisation region is held in the pore typically results in a current blockade in the same window as the current blockade that results from hybridisation of the target polynucleotide to the hybridisation region of the probe that holds the first non-hybridisation region in the pore.

Thus, when a target polynucleotide is present in a sample it will result in a current blockade having one part that is characteristic of the first non-hybridisation region and another part that is characteristic of the second non-hybridisation region. The first and second non-hybridisation regions may be the same or different.

Use of a second non-hybridisation region in conjunction with a second hybridisation region, quadruplex-forming region or double stranded region enables more target polynucleotides to be distinguished using the same number of different non-hybridisation regions. For example, six different non-hybridisation regions, each comprising a different "bar code" may be used to distinguish six different target polynucleotides when each probe in the panel comprises a single hybridisation region and a single non-hybridisation region. However, when each probe in the panel comprises two non-hybridisation regions, 36 different combinations of non-hybridisation regions are possible and so the panel can be used to detect 36 different target polynucleotides.

In at least one of the probes of the panel, and preferably all of the probes, the, or a, hybridisation region is at the end of the probe, which may be the 3' end or the 5' end.

The hybridisation and non-hybridisation regions of a probe may be directly attached, or may be joined by a linker. Any suitable linker may be used. The linker is preferably a polymer. The polymer is preferably a polynucleotide, a polypeptide or a polyethylene glycol (PEG).

In one preferred embodiment, one or more of the probes further comprises an anchor that allows it to be coupled to the membrane.

Hybridisation Region

The hybridisation region specifically binds to a target polynucleotide. Preferably, the hybridisation region binds to the target polynucleotide with an affinity that is at least 10 times, such as at least 50, at least 100, at least 200, at least 300, at least 400, at least 500, at least 1000 or at least 10,000 times, greater than its affinity for other (non-target) polynucleotides, for example under conditions suitable for carrying out the methods described herein. Affinity can be measured using known binding assays, such as those that make use of fluorescence and radioisotopes. Competitive binding assays are also known in the art. Preferably, the hybridisation region does not bind to any other oligonucleotide or polynucleotide (any non-target polynucleotide) by base pairing.

Most preferably, the hybridisation region does not hybridise to any other oligonucleotide or polynucleotide (any non-target polynucleotide) even under high stringency conditions.

The hybridisation region typically comprises a nucleic acid sequence that is at least partially complementary to the target polynucleotide. In a preferred embodiment, the hybridisation region is a polynucleotide such as DNA or RNA. The hybridisation is typically single stranded.

The hybridisation region may have at least 90%, such at least 91%, at least 92%, at least 93%, at least 94%, at least 95%, at least 96%, at least 97%, at least 98%, at least 99% or 100%, nucleotide identity to the complement of the target polynucleotide over the entire length of the target polynucleotide, or a region of at least 10, 20 or 30 nucleotides of the target polynucleotide. The hybridisation region may be identical to the complement of the target polynucleotide over its entire length, or to a region of at least 10, 20 or 30 nucleotides of the target polynucleotide, except for the sites at which one or more natural nucleotides are substituted by one or more non-natural nucleotides.

Different hybridisation regions bind to target polynucleotides to different degrees, e.g. have different binding constants. A hybridisation region that binds more strongly to a target polynucleotide will typically prevent the probe from moving through the pore for a longer time period and this can be identified by measuring the current flowing through the pore. The opposite is also true, e.g. a hybridisation region that binds less strongly to a target polynucleotide will prevent the probe from moving through the pore for less time and this can be identified by measuring the current flowing through the pore.

Strength of binding to the target polynucleotide under the conditions used in a method for determining the presence, absence or amount of two or more target polynucleotides may be decreased by introducing one or more base pair mismatch. In a preferred embodiment, the binding strength of a probe to its target polynucleotide may be adjusted to provide a defined dwell time of the hybridised probe when used in in a method for determining the presence, absence or amount of two or more target polynucleotides as described herein by introducing one or more non-natural nucleotides into the hybridisation region of the probe. The hybridisation region of at least one of the probes comprises one or more non-natural amino acid to increase or decrease the strength of binding, e.g. to increase or decrease the length of time the hybridised probe interacts with the pore.

The site of introduction of the non-natural amino acids may be important for determining the length of time for which a probe remains bound to a target polynucleotide when the non-hybridisation region of the probe is within the barrel of a transmembrane pore. For example, non-natural amino acids that weaken the interaction between the hybridisation region of the probe and the target polynucleotide may be present at the end of the hybridisation region that abuts the non-hybridisation region to promote de-hybridisation and shorten the dwell time of the hybridised probe.

The panel of probes is designed so that the hybridisation regions of each of the probes in the panel remain bound to their respective target polynucleotides for similar periods of time when contacted with a transmembrane pore under an applied potential. This is achieved by introducing at least one non-natural nucleotide into the hybridisation region of one or more probes in the panel. One or more non-natural nucleotides may be introduced into the hybridisation region of some or all of the probes in the panel. For example, from two to 100, such as from 5 to 80 or 10 to 50 probes in the panel may contain one or more non-natural nucleotide. The exact number will depend on the size of the panel and the length and sequences of the hybridisation regions. For example, about 5%, 10%, 20%, 30%, 40%, 50%, 60%, 70%, 80% or 90% of the probes in a panel may comprise one or more non-natural nucleotide.

The hybridisation region can be any length, provided that the required dwell time is achieved, e.g. provided that the dwell times of the probes in the panel when bound to their respective target polynucleotides are similar when contacted with a transmembrane pore under an applied potential. The hybridisation region is typically at least 10 nucleotides in length, such as from about 15 to about 50, from about 20 to about 40 or from about 25 to about 30 nucleotides in length, preferably about 18 to about 25 nucleotides.

All or some of the nucleotides in the hybridisation region may be non-natural nucleotides. A hybridisation region may, for example, comprise from 1 to about 50, such as from 2 to about 40, 3 to about 30 or 5 to about 20 or about 10 to about 15 non-natural nucleotides, such as 6, 7, 8, or 9 non-natural nucleotides, to achieve the desired de-hybridisation. For example, 1%, 2%, 3% 4%, 5%, 10%, 15%, 20% or more, such as up to about 50% of the nucleotides in the hybridisation region may be non-natural. In a panel of probes none, one, two or more of the probes may comprise only natural nucleotides in the hybridisation region provided that at least one such as two or more, e.g. 3, 4, 5, 6, 7, 8, 9, or 10 or more, of the probes comprises a hybridisation region comprising at least one non-natural nucleotide.

A non-natural nucleotide is a nucleotide which is not present in nature. Non-natural nucleotides typically contain a nucleobase, a sugar and at least one phosphate group wherein one of the components of the nucleotide is modified. A non-natural nucleotide may comprise a modified sugar and/or a modified nucleobase. Preferably the non-natural nucleotide comprises a modified sugar or a modified nucleobase. Modified sugars include but are not limited to 2' O-methylribose sugar. The non-natural nucleotide may be a peptide nucleic acid (PNA), a locked nucleic acid (LNA) and an unlocked nucleic acid (UNA), a bridged nucleic acid (BNA) or a morpholino, a phosphorothioate or a methylphosphonate. Non-natural nucleotide modified nucleobases include but are not limited to tricyclic cytosine analogue, 2-aminadenine, 5-methylcytosine, C(5)-propynyl-cytosine, C(5)-propynyluracil, 2-Aminopurine and 6-aza pyrimidine.

A non-natural nucleotide may be one which will hybridise to some degree to all of the nucleotides in the target polynucleotide. A non-natural nucleotide is preferably one which will hybridise to some degree to nucleotides comprising the nucleosides adenosine (A), thymine (T), uracil (U), guanine (G) and cytosine (C).

The non-natural nucleotide may be a universal nucleotide. A universal nucleotide may be included in the hybridisation region, although will compromise specificity. A universal nucleotide may be included in the hybridisation region where it is desired to detect more than one target polynucleotide where it is not necessary to distinguish between similar target polynucleotides. A universal nucleotide is one which will hybridise or bind to some degree to all of the nucleotides in the template polynucleotide. A universal nucleotide is preferably one which will hybridise or bind to some degree to nucleotides comprising the nucleosides adenosine (A), thymine (T), uracil (U), guanine (G) and cytosine (C). The universal nucleotide may hybridise or bind more strongly to some nucleotides than to others. For instance, a universal nucleotide (I) comprising the nucleoside, 2'-deoxyinosine, will show a preferential order of pairing of I-C>I-A>I-G approximately=I-T.

The non-natural nucleotides in the probe may be attached to other non-natural nucleotides in the probe or to natural nucleotides in the probe in any manner. The non-natural nucleotides and natural nucleotides are typically attached by their sugar and phosphate groups as in nucleic acids. The non-natural nucleotides or natural nucleotides may be connected via their nucleobases as in pyrimidine dimers.

The non-natural nucleotides may be introduced into the probes in order to increase the dwell time of the probe when hybridised to its target polynucleotide. The term non-natural nucleotides is intended to include all nucleotides other than guanine, cytosine, threonine and alanine. Non-natural nucleotides include modified or non-canonical bases. Non-natural nucleotides which increase the dwell time include but are not limited to 2-O-methyl-RNA bases. Other non-natural nucleotides include for example locked nucleic acids (LNA), peptide nucleic acids (PNA), bridged nucleic acids (BNA), glycol nucleic acids (GNA), threose nucleic acids (TNA), morpholinos, propenyl deoxy uridine and propenyl deoxycitidine. In fact the nucleotides introduced into the probes may be natural or non-natural as long as the Tm of the duplex is changed to alter/improve dwell time.

The dwell time of the hybridised probe is considered to have been increased if the dwell time for the hybridised probe which contains non-natural nucleotides is greater than the dwell time of a hybridised probe that differs from the hybridised probe which contains non-natural nucleotides only in that it comprises natural nucleotides complementary to the target sequence at the positions of the non-natural nucleotides.

The non-natural nucleotides may be introduced into the probes in order to decrease the dwell time of the probe when hybridised to its target polynucleotide. Non-natural nucleotides which decrease the dwell time of a repeating unit include but are not limited to 2-Aminopurines, Unlocked Nucleic Acid (UNA), phosphorothioates, methylphosphonates and 6-aza pyrimidines. 2-Aminopurine can substitute for dA in an oligonucleotide. It is a naturally fluorescent base that is sensitive to the local environment making it a useful probe for monitoring the structure and dynamics of DNA hairpins and for detecting the base stacking state of a duplex. 2-Aminopurine can be destabilising and can slightly lower the Tm. The effect of UNA on Tm is dependent upon construct, sugar type and location. However, in general UNA reduces Tm by 5-10° C. per replacement. However, too many UNA modifications in an oligonucleotide can impede duplex hybridization. In general, phosphorothioates slightly decrease the Tm of an RNA duplex, methylphosphonates decrease Tm more and UNA will have the largest effect. The dwell time of the hybridised probe is considered to have been decreased if the dwell time for the hybridised probe which contains non-natural nucleotides is less than the dwell time of a hybridised probe that differs from the hybridised probe which contains non-natural nucleotides only in that it comprises natural nucleotides complementary to the target sequence at the positions of the non-natural nucleotides.

The non-natural nucleotide may be an abasic nucleotide. Dwell times may be reduced by including one or more abasic nucleotide in the hybridisation region. Inclusion of an abasic residue will however compromise specificity. An abasic nucleotide may be included in the hybridisation region where it is desired to detect more than one target polynucleotide but is not necessary to distinguish between similar target polynucleotides. An abasic nucleotide is a nucleotide that lacks a nucleobase. The abasic nucleotide typically contains a sugar and at least one phosphate group. The sugar is typically a pentose sugar, such as ribose and deoxyribose. The abasic nucleotide is typically an abasic ribonucleotide or an abasic deoxyribonucleotide. The abasic nucleotide typically contains a monophosphate, diphosphate or triphosphate. Phosphates may be attached on the 5' or 3' side of an abasic nucleotide.

Dwell times may be reduced by including one or more base pair mismatches in the hybridisation region. Inclusion of a base pair mismatch will however compromise specificity. A base pair mismatch may be included in the hybridisation region where it is desired to detect more than one target polynucleotide but is not necessary to distinguish between similar target polynucleotides.

The dwell times may be fine tuned by altering the number of non-natural nucleotides in the hybridisation region and/or by altering the pattern of distribution of the non-natural nucleotides in the hybridisation region. Generally increasing the number of non-natural nucleotides which increase the dwell time in the hybridisation region will further increase the dwell time.

For example, a hybridisation region having non-natural nucleotides, which increase the dwell time, distributed evenly along the length of the hybridisation region will result in a longer dwell time than a hybridisation region having the same number of the same non-natural nucleotides clustered at one end of the hybridisation region. Increasing the number of adjacent non-natural nucleotides, which increase the dwell time in the hybridisation region, in the pattern will further increase the dwell time. For example a hybridisation region having a pattern of non-natural and natural nucleotides with the sequence $Z_X N_Y$ or $N_Y Z_X$, where Z is a non-natural nucleotide and N is a natural nucleotide, in which x is 1 and y is 1 will result in a shorter dwell time than one in which $_X$ is 2 and $_Y$ is 1, and one in which $_X$ is 2 and $_Y$ is 1 will result in a shorter dwell time than one in which $_X$ is 3 and $_Y$ is 1.

The hybridisation region may comprise or consist of a pattern of natural and non-natural nucleotides. The hybridisation region preferably comprises or consists of a pattern of one or more instances of $Z_X N_Y$ and/or $N_Y Z_X$ where Z is a non-natural nucleotide and N is a natural nucleotide. The pattern may be regular or irregular. The hybridisation region may comprise, or consist of, one or more instances of $Z_X N_Y$. The hybridisation region may comprise, or consist of, one or more instances of $N_Y Z_X$. The hybridisation region may comprise, or consist of, one or more instances of $Z_X N_Y$ and $N_Y Z_X$. The hybridisation region preferably comprise, or consist of, 2, 3, 4, 5, 6, 7, 8, 9 or 10 instances of $Z_X N_Y$ and/or $N_Y Z_X$.

If there are two or more non-natural nucleotides in the hybridisation region, the non-natural nucleotides may be the same or different. Preferably, all of the instances of Z in the hybridisation region are the same type of non-natural nucleotide.

N is typically complementary to one of the nucleotides in the target polynucleotide. Z is preferably complementary to one of the nucleotides in the target polynucleotide. It is straightforward for a person skilled in the art to identify nucleotides that are complementary. A nucleotide is complementary to another nucleotide if it hybridises through base pairing, preferably Watson and Crick base pairing, to the nucleotide. A complementary nucleotide may hybridise to other nucleotides with which it is not complementary, but to a smaller degree than it hybridises to the nucleotide with which it is complementary. N preferably comprises one of the nucleobases adenine (A), uracil (U), guanine (G) or cytosine (C). Alternatively, N preferably comprises the nucleobases A, thymine (T), G or C. A is complementary to T or U and vice versa. G is complementary to C and vice versa.

For $Z_X N_Y$ and/or $N_Y Z_X$, X is 1, 2, 3, 4, 5 or 6 and Y is 1, 2, 3, 4, 5 or 6. The pattern of $Z_X N_Y$ and/or $N_Y Z_X$ is preferably regular. This allows the non-natural nucleotides to be evenly distributed throughout the hybridisation region. In particular, X and/or Y may be the same in different instances of $Z_X N_Y$ and/or $N_Y Z_X$. Both X and Y are preferably the same in different instances of $Z_X N_Y$ and/or $N_Y Z_X$, i.e. in different hybridisation regions in probes of the panel. For example, in at least one instance of $Z_X N_Y$ and/or $N_Y Z_X$: (i) X is 1 and Y is 1; (ii) X is 2 and Y is 2; (iii) X is 3 and Y is 3; (iv) X is 4 and Y is 4; (v) X is 5 and Y is 5; (vi) Y is 1 and Z is 2, 3, 4, 5 or 6; (vii) Y is 2, 3, 4, 5 or 6 and Z is 1; (viii) Y is 2 and Z is 2, 3, 4, 5 or 6; (viii) Y is 2, 3, 4, 5 or 6 and Z is 2; (ix) Y is 3 and Z is 3, 4, 5 or 6; or (x) Y is 3, 4, 5, or 6 and Z is 3. At least one, and optionally all, of the hybridisation regions may have a regular pattern.

One or more, optionally all, of the hybridisation regions in the probes in the panel may comprise, or consist of:
(a) ZN-ZN-ZN-ZN-ZN-ZN;
(b) NZ-NZ-NZ-NZ-NZ-NZ;
(c) ZZNN-ZZNN-ZZNN;
(d) NNZZ-NNZZ-NNZZ;
(e) ZZZNNN-ZZZNNN;
(f) NNNZZZ-NNNZZZ;
(g) ZZZZNNNN-ZZZZNNNN;
(h) NNNNZZZZ-NNNNZZZZ;
(i) ZN-ZN-ZN-ZN;

(j) NZ-NZ-NZ-NZ;
(k) ZZNN-ZZNN;
(l) NNZZ-NNZZ;
(m) ZZZZNNNN;
(n) NNNNZZZZ;
(o) ZZN-ZZN-ZZN;
(p) NNZ-NNZ-NNZ;
(q) ZZZN-ZZZN-ZZZN-ZZZN;
(r) NNNZ-NNNZ-NNNZ-NNNZ;
(s) ZZZN-ZZZN-ZZZN; or
(t) NNNZ-NNNZ-NNNZ
(u) NNNNZ-NNNNZ-NNNNZ
(v) ZNNNN-ZNNNN-ZNNNN
(w) NNNNNZ-NNNNNZ-NNNNNZ
(x) ZNNNNN-ZNNNNN-ZNNNNN.

In the above, "-" is used for presentation purposes to separate the repeating units of $Z_X N_Y$ or $N_Y Z_X$. The same applies below.

The pattern of $Z_X N_Y$ and/or $N_Y Z_X$ may be irregular. In particular, X and/or Y may be different in different instances of $Z_X N_Y$ and/or $N_Y Z_X$. X and Y are more preferably different in different instances of $Z_X N_Y$ and/or $N_Y Z_X$, i.e. in different hybridisation regions in probes of the panel. For example, in at least one instance of $Z_X N_Y$ and/or $N_Y Z_X$, X is 2 and Y is 1; X is 1 and Y is 2; X is 3 and Y is 1; or X is 1 and Y is 3. At least one, and optionally all, of the hybridisation regions may have an irregular pattern.

One or more, optionally all, of the hybridisation regions in the probes in the panel may comprise, or consist of:
(aa) NZ-ZNN-ZZNN-ZZN;
(bb) ZN-NZZ-NNZZ-NNZ;
(cc) NNZZ-ZZNN-NNNZZZ-ZNN;
(dd) ZZNN-NNZZ-ZZZNNN-NZZ;
(ee) NNZZ-ZZNN;
(ff) ZZNN-NNZZ;
(gg) NZZ-NNZ-ZNN-ZZN;
(hh) ZNN-ZZN-NZZ-NNZ;
(ii) NZZ-NNZ-ZN; or
(jj) ZNN-ZZN-NZ.

The panel of probes typically comprises probes which contain hybridisation regions comprising different patterns of natural and non-natural nucleotides, which may be regular or irregular and which may include at least one hybridisation region comprising only natural nucleotides, in order to optimise the dwell times of the probes in the panel, i.e. so that all of the probes in the panel have a dwell time within a defined window when their respective target polynucleotides are present in the sample.

Defined Dwell Time Window

Dwell times are considered to be similar, or approximately the same, if the dwell times are within 10 seconds or less of each other, preferably within 5 seconds, 2 seconds, 1 second, 0.5 seconds, 0.2 seconds or 0.1 seconds or less of each other. The dwell times are most preferably within 1 second or less of each other.

In the method for determining the presence, absence or amount of two or more target polynucleotides, the durations of the current blockades caused by at least two of the probes, such as 3, 4, 5 6, 10 or all of the probes, in the panel hybridised to their respective target polynucleotides may be within 10 seconds or less of each other, preferably within 5 seconds or less, preferably within 2 seconds or less, 1 second or less, 0.5 seconds or less, 0.2 seconds or less or 0.1 seconds of each other.

Thus, in some embodiments, the defined window may have an overall width of 10 seconds, 5 seconds, 4 seconds, 3 seconds, 2 seconds, 1 second, 0.5 seconds or 0.2 seconds.

For example a 10 second window may capture current blockades of from 0.01 to 10 seconds, 1 second to 11 seconds, 5 seconds to 15 seconds etc. Current blockades having a duration that is shorter than those of the defined window, or longer than those of the defined window, are not measured.

The term "measured" is intended to mean detecting and analysing. All current blockades resulting from interactions of components of the sample with the pore will be detected. However, only current blockades falling within the window of interest will be measured in a method for determining the presence, absence or amount of two or more target polynucleotides.

In one embodiment, substantially all of the current blockades due to the interaction of the hybridised probes with the pore occur within the window and/or the majority of current blockades that occur outside the window are due to the additional components in the sample.

Non-Hybridisation Region

The non-hybridisation region comprises a part which is capable of entering the pore. The non-hybridisation region is typically a linear molecule that is capable of entering and passing through the barrel or channel of the pore. When the non-hybridisation region enters the pore, it affects the current flowing through the pore in a manner that is specific for the part of the non-hybridisation region that is present in the barrel or channel.

The non-hybridisation region has different effects on the current flowing through the pore depending on whether or not the probe is hybridised to its target polypeptide. The non-hybridisation region in each probe affects the current flowing through the pore in one way when the target polynucleotide is not bound to the probe and affects the current flowing through the pore in a different way when the target polynucleotide is bound to the probe. This allows the presence or absence of the target polynucleotide to be determined using the method.

Hybridisation of the probe to the target polynucleotide affects the time taken for the probe to move through the pore. In the absence of the target polynucleotide, the probe passed rapidly through the pore. When the pore is hybridised to its target polynucleotide, the passage of the probe through the pore is hindered.

Typically, when the probe is not hybridised to its target polynucleotide, it passes rapidly through the pore under an applied potential. Current blockades resulting from unhybridised probes in the panel typically have short durations that fall outside the defined window in which current blockades are measured.

Without wishing to be bound by theory, for a short while, the movement of the entire probe through the pore is prevented (i.e. delayed) by the hybridised target polynucleotide. Double stranded polynucleotides are typically too large to move through the barrel or channel of the pore. After a short while, the target polynucleotide is released from the probe under the influence of the potential and the entire probe is able to move through the pore. Once the probe has exited the pore, the current flowing through the pore returns to the level seen in the absence of the sample and the panel of probes. Each hybridised probe affects the current flowing through the pore for a specific amount of time ("dwell time"). The duration of the current blockade caused by the hybridized probe when the target polynucleotide is present in the sample can be controlled by modifying the hybridisation region of the probe as discussed herein.

The current blockades resulting from the interaction of each of the hybridised probes may be distinguished based on differences in the current blockades resulting from differences (e.g. differences in signal level, signal pattern, signal deviations) between the non-hybridisation regions of the probes, and optionally the hybridisation regions of the probe.

The pore comprises a barrel or channel and may comprise a vestibule. The barrel or channel typically allows the non-hybridisation region of the probe to enter, but does not allow the double stranded hybridised region of the probe, e.g. the region of the hybridised pore comprising the hybridisation region and the target polynucleotide to enter. For a particular pore, non-hybridisation regions that are suitable for inclusion in the panel of probes can be designed based on, for instance, known lengths of the barrel or channel, and where present the vestibule, of the pore.

The non-hybridisation region of the probe may comprise any of the nucleotides discussed herein. In some embodiments, the non-hybridisation region has an abasic leader sequence, where the leader sequence is the first region of the non-hybridisation region to pass into the pore. The leader sequence is typically single stranded and may, for example, comprise from 3 to 20, such as from 5 to 15 or 8 to 12, e.g. 10 nucleotides. In some embodiments, the non-hybridisation region comprises at least two adjacent abasic residues, for example 3, 4, 5, 6, 7 or more adjacent abasic residues.

In preferred embodiments, the non-hybridisation region comprises a polymer, for example a linear polymer. The polymer is capable of entering the pore and affecting the current flowing through the pore. The polymer is preferably a polynucleotide, a polypeptide, a polysaccharide or a polyethylene glycol (PEG). The non-hybridisation region may comprise different combinations of polymers.

The non-hybridisation region may be any length. The tail preferably comprises a polynucleotide from about 7 to about 70 nucleotides in length, such as from about 10 to about 60, from about 20 to about 50 or from about 30 to about 40 nucleotides in length.

The non-hybridisation region may be a tail region as described in WO 2013/121201.

The non-hybridisation region preferably comprises at least one single stranded polynucleotide or polynucleotide region. Single stranded polynucleotides are useful in the non-hybridisation region because they can pass through the pore and can easily be divided into at least two different regions that affect the current flowing through the pore in different ways. For instance, different regions of a polynucleotide having different sequences typically affect the current flowing through the pore in different ways. The at least two different regions preferably correspond to at least two stretches of different nucleotides. For instance, the single stranded polynucleotide region may comprise a stretch of adenine nucleotides and a stretch of abasic nucleotides. Each stretch will affect the current flowing through the pore in a different way. Alternatively, the at least two stretches of different nucleotides are different polynucleotide barcodes. Polynucleotide barcodes are well-known in the art (Kozarewa, I. et al., (2011), *Methods Mol. Biol.* 733, p 279-298). A barcode is a specific sequence of polynucleotide that affects the current flowing through the pore in a specific and known manner.

The non-hybridisation region may comprise one or more non-natural nucleotides. For instance, T k-mers (i.e. k-mers in which the central nucleotide is thymine-based, such as TTA, GTC, GTG and CTA) typically have the lowest current states. Modified versions of T nucleotides may be introduced into the probe, particularly into the non-hybridisation region, to reduce the current states further and thereby increase the total current range seen when the modified polynucleotides moves through the pore.

G k-mers (i.e. k-mers in which the central nucleotide is guanine-based, such as TGA, GGC, TGT and CGA) tend to be strongly influenced by other nucleotides in the k-mer and so modifying the G nucleotides in the probe, particularly in the non-hybridisation region, may help them to have more independent current positions.

Including three copies of the same nucleotides instead of three different nucleotides may facilitate characterisation because it is then only necessary to map, for example, 3-nucleotide k-mers in the probe. However, such modifications do reduce the information provided by the probe.

Including one or more abasic nucleotides results in characteristic current spikes. This allows the clear highlighting of the positions of the one or more nucleotides in the probe.

In some embodiments, the non-hybridisation region is unrelated to any of the target or non-target polynucleotides present in a sample, or that might be expected to be in a sample. For example, the non-hybridisation region may be less than about 70%, such as less than about 50%, less than about 30%, less than about 20% or less than about 10% complementary to any portion of a target polynucleotide.

Quadruplex

One or more, such as all, the probes in the panel may comprise a sequence capable of forming a quadruplex between two non-hybridisation regions as defined above. The quadruplex-forming sequence also does not hybridise to a target polynucleotide. A quadruplex is a three dimensional structure formed from four sequence strands.

The quadruplex is not capable of translocating or moving through the narrowest part of the pore. The quadruplex is wider than the narrowest part of the pore. For example, the narrowest part of wild-type α-HL pore is 1.3 nm is diameter. The narrowest part of α-HL-NN pore is 1.5 nm in diameter. In embodiments using these pores, the quadruplex preferably has a width of greater than 1.3 nm, such as greater than 1.5 nm, such as greater than 2 nm, greater than 3 nm or greater than 5 nm. A person skilled in the art will be able to design a suitably sized quadruplex for the pore being used. The quadruplex-forming sequence is capable of translocating or moving through the narrowest part of the pore when it is not formed into a quadruplex.

The quadruplex-forming sequence is preferably a polynucleotide. It may be any of the nucleotides discussed herein. The quadruplex-forming sequence may, for example, Have a length of from about 10 to about 50 nucleotides, such as from about 12 to about 40 nucleotides, from about 14 to about 30 nucleotides or from about 16 to about 20 nucleotides.

The quadruplex may be any type of quadruplex. The quadruplex may be an intermolecular quadruplex, such as a bimolecular quadruplex or a tetramolecular quadruplex. The quadruplex-forming sequence is preferably capable of forming an intramolecular quadruplex.

The quadruplex-forming sequence is preferably capable of forming G-quadruplexes (also known as G-tetrads or G4-DNA). These are polynucleotide sequences that are rich in guanine and are capable of forming a four-stranded structure. Four guanine bases can associate through Hoogsteen hydrogen bonding to form a square planar structure called a guanine tetrad, and two or more guanine tetrads can stack on top of each other to form a G-quadruplex. The quadruplex structure is further stabilized by the presence of a cation, especially potassium, which sits in a central channel between each pair of tetrads. Forming G-quadruplexes is well known in the art (Marathias and Bolton, *Nucleic Acids Research*, 2000; 28(9): 1969-1977; Kankia and Marky, *J. Am. Chem. Soc.* 2001, 123, 10799-10804; and Marusic et al., *Nucleic Acids Research*, 2012, 1-11).

The quadruplex-forming sequence more preferably comprises the sequence Ga followed by Nb followed by Gc followed by Nd followed by Ge followed by Nf followed by Gg, wherein G is a nucleotide comprising guanine, wherein a, c, e and g are independently selected from 1, 2, 3, 4 and 5, wherein N is any nucleotide and wherein b, d and f are from 2 to 50. The values of a, c, e and g may be identical. G is preferably guanosine monophosphate (GMP), cyclic guanosine monophosphate (cGMP), deoxyguanosine monophosphate (dGMP), dideoxyguanosine monophosphate, N2-methyl-GMP, N2-methyl-cGMP, N2-methyl-dGMP, N2-methyl-dideoxyguanosine monophosphate, N2-methyl-06-methyl-GMP, N2-methyl-06-methyl-cGMP, N2-methyl-06-methyl-dGMP, N2-methyl-06-methyl-dideoxyguanosine monophosphate, 2'-O-methyl-GMP, 2'-O-methyl-cGMP, 2'-O-methyl-dGMP, 2'-O-methyl-dideoxyguanosine monophosphate, 6-thio-GMP, 6-thio-cGMP, 6-thio-dGMP, 6-thio-dideoxyguanosine monophosphate, 7-methyl-GMP, 7-methyl-cGMP, 7-methyl-dGMP, 7-methyl-dideoxyguanosine monophosphate, 7-deaza-GMP, 7-deaza-cGMP, 7-deaza-dGMP, 7-deaza-dideoxyguanosine monophosphate, 8-oxo-GMP, 8-oxo-cGMP, 8-oxo-dGMP or 8-oxo-dideoxyguanosine monophosphate.

Suitable quadruplex-forming sequences are disclosed in WO 2014/072703. The quadruplex-forming sequence preferably comprises the sequence shown in nucleotides 28 to 42 of SEQ ID NO: 1.

Since the quadruplex is incapable of translocating through the narrowest part of the pore, it acts like a brake and holds region one of the non-hybridisation regions in the narrowest part of the pore. The non-hybridisation region then results in a distinctive current which identifies the probe. After a short while, the quadruplex will typically destabilise under the influence of the applied potential and unfold. The braking action of the quadruplex is therefore typically temporary. The non-hybridisation region is typically only held in the narrowest part of the pore temporarily. The unfolded quadruplex-forming sequence translocates or moves through the pore under the influence of the applied potential.

Double-Stranded Region

Double stranded polynucleotides cannot pass through the pore, and so a double stranded region can be included in the probes in the panel in place of a quadruplex-forming sequence or second hybridisation region. In practice, the probes may be generated as single stranded molecules incorporating, between the two non-hybridisation regions, one strand of the double stranded region. The other stand of the double stranded region may then be hybridised with the probe prior to contacting the sample with the panel of probes or when the panel of probes is contacted with the sample. The double stranded region typically has the same sequence in each of the probes in the panel. The presence of such a double stranded region does not prevent the probe from moving through the pore, but instead simply delays the movement of the probe through the pore as one of the strands in the double stranded region is stripped from the probe under the influence of the potential. Such a delay can be seen as the current flowing through the pore is measured. The duration of the current blockade typically falls within the same window of current blockade durations as the current blockade resulting from the delay caused by the hybridisation of the probes in the panel to their respective target polynucleotides.

The duration of current blockade produced by the double stranded region may be adjusted to fit within a defined time window by, for example, altering the length of the double stranded region, altering the degree of complementarity between the strands of the double stranded region and/or altering the composition of the double stranded region, such as by incorporating non-natural nucleotides as described herein for the hybridisation region.

The double stranded region may, for example, have a length of from about 10 to about 50 nucleotides, such as from about 12 to about 40 nucleotides, from about 14 to about 30 nucleotides or from about 16 to about 20 nucleotides.

The double stranded region may, for example, comprise a first strand and a second strand wherein the first strand is at least 70%, such at least 80%, at least 90%, at least 95%, at least 96%, at least 97%, at least 98%, at least 99% or 100% complementary to the second strand. Including one or more double stranded polynucleotide regions in each probe region increases the number of possible signals that can be obtained from a panel of probes and hence increases the number of target polynucleotides that can be assayed using the method of the invention.

A double stranded polynucleotide region may, for example, be used to hold a specific region of the non-hybridisation region, such as a barcode, that is indicative of the probe in the barrel or channel of the pore so that it may be read in accordance with the invention.

Linkers

The different regions of the probe described herein may be joined directly or by one or more linkers. In some embodiments, a linker can be a peptidyl linker or oligonucleotide linker. In some embodiments, any suitable spacer may be used as a linker. Examples of a suitable spacers include is idSp (1',2'-dideoxyribose) or iSpC3 (an internal C3 spacer) and other suitable spacers are known in the art (see, for example, idtdna.com/Site/Catalog/Modifications/Category/6). Another example is triethylene glycol (TEG). One or more, such as 2, 3 or 4 spacers, such as idSp, iSpC3 and/or TEG, may be used to join adjacent regions of the probe.

Nucleotides

Each probe in the panel of probes comprises a nucleotide sequence. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hydroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

If the probe is DNA, the probe may comprise one or more non-natural nucleotides that comprise a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the probe is RNA, the probe may comprise one or more non-natural nucleotides which differ from adenine, guanine, uracil, cytosine or methylcytosine and/or comprises a nucleoside which differ from adenosine, guanosine, uridine, cytidine or methylcytidine. The different nucleobase and/or nucleoside is/are capable of hybridising to one or more of the nucleotides in the target polynucleotide when present in the hybridization region. Commercially available nucleosides include, but are not limited to, 2,6-Diaminopurine-2'-deoxyriboside, 2-Aminopurine-2'-deoxyriboside, 2,6-Diaminopurine-riboside, 2-Aminopurine-riboside, Pseudouridine, Puromycin, 2,6-Diaminopurine-2'-O-methylriboside, 2-Aminopurine-2'-O-methylriboside and Aracytidine. The non-natural nucleotide may comprise any of these nucleosides.

The non-natural nucleotide may be a universal nucleotide. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The non-natural nucleotide may comprise a chemical atom or group absent from the natural nucleotide it is replacing. The chemical group is preferably a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom.

Commercially available nucleosides comprising chemical groups which are absent from naturally-occurring nucleosides include, but are not limited to, 6-Thio-2'-deoxyguanosine, 7-Deaza-2'-deoxyadenosine, 7-Deaza-2'-deoxyguanosine, 7-Deaza-2'-deoxyxanthosine, 7-Deaza-8-aza-2'-deoxyadenosine, 8-5'(5'S)-Cyclo-2'-deoxyadenosine, 8-Amino-2'-deoxyadenosine, 8-Amino-2'-deoxyguanosine, 8-Deuterated-2'-deoxyguanosine, 8-Oxo-2'-deoxyadenosine, 8-Oxo-2'-deoxyguanosine, Etheno-2'-deoxyadenosine, N6-Methyl-2'-deoxyadenosine, O6-Methyl-2'-deoxyguanosine, O6-Phenyl-2'deoxyinosine, 2'-Deoxypseudouridine, 2-Thiothymidine, 4-Thio-2'-deoxyuridine, 4-Thiothymidine, 5' Aminothymidine, 5-(1-Pyrenylethynyl)-2'-deoxyuridine, 5-(C2-EDTA)-2'-deoxyuridine, 5-(Carboxy)vinyl-2'-deoxyuridine, 5,6-Dihydro-2'-deoxyuridine, 5.6-Dihydrothymidine, 5-Bromo-2'-deoxycytidine, 5-Bromo-2'-deoxyuridine, 5-Carboxy-2'-deoxycytidine, 5-Fluoro-2'-deoxycytidine, 5-Formyl-2'-deoxycytidine, 5-Hydroxy-2'-deoxycytidine, 5-Hydroxy-2'-deoxyuridine, 5-Hydroxymethyl-2'-deoxycytidine, 5-Hydroxymethyl-2'-deoxyuridine, 5-Iodo-2'-deoxycytidine, 5-Iodo-2'-deoxyuridine, 5-Methyl-2'-deoxycytidine, 5-Methyl-2'-deoxyisocytidine, 5-Propynyl-2'-deoxycytidine, 5-Propynyl-2'-deoxyuridine, 6-O-(TMP)-5-F-2'-deoxyuridine, C4-(1,2,4-Triazol-1-yl)-2'-deoxyuridine, C8-Alkyne-thymidine, dT-Ferrocene, N4-Ethyl-2'-deoxycytidine, O4-Methylthymidine, Pyrrolo-2'-deoxycytidine, Thymidine Glycol, 4-Thiouridine, 5-Methylcytidine, 5-Methyluridine, Pyrrolocytidine, 3-Deaza-5-Aza-2'-O-methylcytidine, 5-Fluoro-2'-O-Methyluridine, 5-Fluoro-4-O-TMP-2'-O-Methyluridine, 5-Methyl-2'-O-Methylcytidine, 5-Methyl-2'-O-Methylthymidine, 2',3'-Dideoxyadenosine, 2',3'-Dideoxycytidine, 2',3'-Dideoxyguanosine, 2',3'-Dideoxythymidine, 3'-Deoxyadenosine, 3'-Deoxycytidine, 3'-Deoxyguanosine, 3'-Deoxythymidine and 5'-O-Methylthymidine. The non-natural nucleotide may comprise any of these nucleosides. The non-natural nucleotide is most preferably 2'-fluoro-2'-deoxyadenosine or 5-carboxy-2'-deoxycytidine.

Alternatively, the non-natural nucleotide preferably lacks a chemical group or atom present in the natural nucleotide it is replacing.

The non-natural nucleotide preferably has an altered electronegativity compared with the one or more nucleotides being replaced. The non-natural nucleotide having an altered electronegativity preferably comprises a halogen atom. The halogen atom may be attached to any position on the non-natural nucleotide, such as the nucleobase and/or the sugar. The halogen atom is preferably fluorine (F), chlorine (Cl), bromine (Br) or iodine (I). The halogen atom is most preferably F or I.

Commercially available nucleosides comprising a halogen include, but are not limited to, 8-Bromo-2'-deoxyadenosine, 8-Bromo-2'-deoxyguanosine, 5-Bromouridine, 5-Iodouridine, 5-Bromouridine, 5-Iodouridine, 5'-Iodothymidine and 5-Bromo-2'-O-methyluridine. The non-natural nucleotide may comprise any of these nucleosides.

Any of the nucleotides mentioned in the Examples may also be used in the methods described herein.

Distinctive Currents

Each probe (i.e. each type of probe) affects the current flowing through the pore in a distinctive manner. In other words, a probe affects the current flowing through the pore in a manner that can be distinguished or differentiated from the way in which a different probe affects the current flowing through the pore. This allows the identity of each probe (i.e. each type of probe) to be determined in accordance with the invention. The binding of the probe to a target polynucleotide can then be measured as discussed above. Since the identity of each probe and the binding of each probe to a target polynucleotide can be measured, the presence or absence of each target polynucleotide can be determined.

Each probe (i.e. each type of probe) preferably affects the current flowing through the pore in a distinctive manner when it binds to a target polynucleotide. In other words, the binding of a target polynucleotide to a probe preferably affects the current flowing through the pore in a manner that can be distinguished or differentiated from the way in which a different probe affects the current flowing through the pore when it binds a target polynucleotide. The different probes may bind to the same target polynucleotide.

The distinctive manner may concern the extent to which the current flowing through the pore is affected, i.e. a change in amount of current that flows through the pore as the probe binds to its target polynucleotide, and/or the time for which the current is affected by binding of the probe to its target polynucleotide (the "dwell time"). The value of the current disruption is of greater value than the dwell time as the former provides more distinct signatures, whereas the hybridisation regions of the probes have been designed such that the dwell times of the probes in the panel when hybridised to their respective target polynucleotides are within a defined window. This means that the dwell times of the various hybridised probes have a narrow distribution. The distinctive manner may concern the extent to which the variance of the current flowing the through the pore is affected. The variance may increase or decrease as a result of the binding of a target polynucleotide to a probe.

A panel of probes may be designed to give well separated current blockade clusters when hybridised to their respective target polynucleotides and analysed using a nanopore. Examples of current features that may be used to identify probes hybridised to particular target polynucleotides include current blockade length (or dwell), the "variation" or standard deviation and/or the current blockade noise. This is exemplified in Example 4 of the application. When the panel of probes is hybridised to the target polynucleotides and contacted with a nanopore, a cluster corresponding to each of the duplexes formed by hybridisation of a target polynucleotide to its probe is visible. This is illustrated for a particular example in FIG. 4. The current blockades formed by all of the duplexes are detected within a defined window. Only these current blockades occurring with the defined window are measured and put forward for further analysis.

Control experiments may be carried out to ensure that different probes have different effects on the current flowing through the pore when the probe binds to a target polynucleotide. Such control experiments can also help to determine the effect a particular probe has on the current flowing through the pore when the probe is bound to its target polynucleotide. Results from carrying out the method of the invention on a test sample can then be compared with those derived from such control experiments in order to determine whether a particular target polynucleotide is present or absent in the test sample, or to determine the amount of the polynucleotide in the test sample.

The distinctiveness between probes can be achieved via differences in their lengths. Longer probes will affect the current flowing through a pore for more time, i.e. longer dwell time. Shorter probes will affect the current flowing through the pore for less time, i.e. shorter dwell time.

In preferred embodiments, the non-hybridisation region, or a part thereof, is briefly held in the barrel or channel of the pore when a probe binds to its target polynucleotide. When the probe comprises a second non-hybridisation region separated from the first by a second hybridisation region, a quadruplex-forming region or a double stranded region, the second-non-hybridisation region is held in the pore either before or after the first hybridisation region, depending on the order of the regions in the probe. Differences between the specific regions of different probes in the panel, such as the presence of different polymers and different polynucleotide species, affect the current flowing through the pore. For example, different sequences of the same type of polymer, for example where one sequence comprises two or more adjacent abasic residues, can also account for the distinctiveness between the probes. It is straightforward to design a panel of non-hybridisation regions that have the required distinctiveness as described, for example in WO 2013/121201.

Where the probe comprises a quadruplex-forming region or a double stranded region, the current blockade has two phases if the relevant target polynucleotide is present in the sample, but only one phase if the target polynucleotide is not present.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936). Suitable DNA origami pores are disclosed in WO2013/083983.

The transmembrane pore is preferably a transmembrane protein pore. A transmembrane protein pore is a polypeptide or a collection of polypeptides that permits hydrated ions, such as polynucleotide, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore is preferably derived from CsgG, more preferably from CsgG from E. coli Str. K-12 substr. MC4100. Such a pore will be oligomeric and typically comprises 7, 8, 9 or 10 monomers derived from CsgG. The pore may be a homo-oligomeric pore derived from CsgG comprising identical monomers. Alternatively, the pore may be a hetero-oligomeric pore derived from CsgG comprising at least one monomer that differs from the others. Examples of suitable CsgG pores are described in WO/2016/034591, WO 2017/149316, WO 2017/149317 and WO 2017/149318.

The transmembrane protein pore typically comprises a barrel or channel through which the ions may flow. The subunits of the pore typically surround a central axis and contribute strands to a transmembrane R barrel or channel or a transmembrane α-helix bundle or channel.

The barrel or channel of the transmembrane protein pore typically comprises amino acids that facilitate interaction with an analyte, such as a nucleotide, polynucleotide or nucleic acid. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as Mycobacterium smegmatis porin (Msp), for example MspA, MspB, MspC or MspD, CsgG, outer membrane porin F (OmpF), outer membrane porin G (OmpG), outer membrane phospholipase A and Neisseria autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin.

The transmembrane pore may be derived from or based on Msp, α-hemolysin (α-HL), lysenin, CsgG, ClyA, Spl and haemolytic protein fragaceatoxin C (FraC). The transmembrane protein pore is preferably derived from CsgG, more preferably from CsgG from E. coli Str. K-12 substr. MC4100. Suitable pores derived from CsgG are disclosed in WO 2016/034591. The transmembrane pore may be derived from lysenin. Suitable pores derived from lysenin are disclosed in WO 2013/153359.

The wild type α-hemolysin pore is formed of 7 identical monomers or sub-units (i.e., it is heptameric). The α-hemolysin pore may be α-hemolysin-NN or a variant thereof. The variant preferably comprises N residues at positions E111 and K147. The sequence of one monomer or sub-unit of α-hemolysin-NN is shown in SEQ ID NO: 3.

A monomer derived from α-HL-NN typically comprises the sequence shown in SEQ ID NO: 3 or a variant thereof. A variant of SEQ ID NO: 3 is a polypeptide that has an amino acid sequence which varies from that of SEQ ID NO: 3 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and WO 2006/100484.

Over the entire length of the amino acid sequence of SEQ ID NO: 3, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 3 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemicophysical properties rather than frequency of substitution over evolutionary time scales (e.g. charge).

Amino acid substitutions may be made to the amino acid sequence of SEQ ID NO: 3, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

The transmembrane protein pore is preferably derived from Msp, more preferably from MspA. Suitable pores derived from MspA are disclosed in WO 2012/107778.

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Braha et al. (1997) Chem Biol. 4(7): 497-505).

The pore may be labelled with a revealing label. The revealing label may be any suitable label which allows the pore to be detected. Suitable labels include, but are not limited to, fluorescent molecules, radioisotopes, e.g. $^{125}$I $^{35}$S, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Coupling

In some embodiments, the probes may comprise one or more anchors which are capable of coupling to the membrane. In some embodiments, the method for determining the presence, absence or amount of two or more target polynucleotides may further comprise coupling the probes to the membrane using the one or more anchors.

The anchor comprises a group which couples (or binds) to the probe and a group which couples (or binds) to the membrane. Each anchor may covalently couple (or bind) to the probe and/or the membrane.

The probe may be coupled to the membrane using any number of anchors, such as 2, 3, 4 or more anchors. For instance, the probe may be coupled to the membrane using two anchors each of which separately couples (or binds) the probe to the membrane.

The one or more anchors may comprise one or more polynucleotide binding proteins.

If the membrane is an amphiphilic layer, such as a triblock copolymer membrane, the one or more anchors preferably comprise a polypeptide anchor and/or a hydrophobic anchor that can be inserted into the membrane. The hydrophobic anchor is preferably a lipid, fatty acid, sterol, carbon nanotube, polypeptide, protein or amino acid, for example cholesterol, palmitate or tocopherol. In preferred embodiments, the anchor is cholesterol. The anchor is preferably not coupled to the membrane via the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed below. Any proportion of the membrane components may be functionalised, for example at least 0.01%, at least 0.1%, at least 1%, at least 10%, at least 25%, at least 50% or 100%.

The probes may be coupled directly to the membrane. The one or more anchors used to couple a probe to the membrane preferably comprise a linker. The one or more anchors may comprise one or more, such as 2, 3, 4 or more, linkers. One linker may be used to couple more than one, such as 2, 3, 4, or more, probes to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The probe may hybridise to a complementary sequence on the circular polynucleotide linker.

The one or more anchors or one or more linkers may typically comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane, may be the part of the probe or may be used to couple (or bind) to a polynucleotide probe.

Cross-linkage of polynucleotides can be avoided using a "lock and key" arrangement. Only one end of each linker may react together to form a longer linker and the other ends of the linker each react with the polynucleotide or membrane respectively. Such linkers are described in WO 2010/086602.

The coupling is preferably transient. In other words, the coupling may be such that the probe may decouple from the membrane when interacting with the pore. The probe may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, the probe is coupled to an amphiphilic layer such as a triblock copolymer membrane or lipid bilayer. Coupling of nucleic acids to synthetic lipid bilayers has been carried out previously with various different tethering strategies. These are summarised in Table 1 below.

TABLE 1

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucleotides to lipid membrane assemblies." *J Am Chem Soc* 126(33): 10224-5 |
| Surfactant (e.g. Lipid, Palmitate, etc.) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

An anchor comprising thiol, biotin or a surfactant may be used in conjunction with a component that can be cut or broken down to achieve transient coupling of the probe to the membrane.

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the probe to the membrane. Therefore, when coupling is used in a method of the invention, all of the probes in the panel are coupled to the membrane in the same manner.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. It may also be possible that anchors may be directly added to polynucleotides using terminal transferase with suitably modified nucleotides (e.g. cholesterol or palmitate).

The one or more anchors may couple the probe to the membrane via hybridisation. The hybridisation may be present in any part of the one or more anchors, such as between the one or more anchors and the probe, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more anchors may hybridise to the polynucleotide. The one or more anchors may hybridise directly to the non-hybridisation region of the probe. Alternatively, the one or more anchors may be hybridised to one or more, such as 2 or 3, intermediate polynucleotides (or "splints") which are hybridised to the probe.

The one or more anchors can be incorporated during the chemical synthesis of the probe. For instance, the probe can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

Ideally, the probe is coupled to the membrane without having to functionalise the probe. This can be achieved by coupling the one or more anchors, such as a polynucleotide binding protein or a chemical group, to the membrane and allowing the one or more anchors to interact with the probe or by functionalizing the membrane. The one or more anchors may be coupled to the membrane by any of the methods described herein. In particular, the one or more anchors may comprise one or more linkers, such as maleimide functionalised linkers.

The one or more anchors can comprise any group that couples to, binds to or interacts with single stranded polynucleotides, specific nucleotide sequences within the probe or patterns of modified nucleotides within the probe, or any other ligand that is present on the probe.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins.

The one or more anchors can comprise any group which couples to, binds to, intercalates with or interacts with a polynucleotide. The group may intercalate or interact with the probe via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A probe may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex.

In this embodiment at least 1%, at least 10%, at least 25%, at least 50% or 100% of the membrane components may be functionalised.

Where the one or more anchors comprise a protein, they may be able to anchor directly into the membrane without further functionalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the probes before delivery to the membrane, but the one or more anchors may be contacted with the membrane and subsequently contacted with the probes.

In another aspect the probe may be functionalised, using methods described herein, so that it can be recognised by a specific binding group. Specifically the probe may be functionalised with a ligand such as biotin (for binding to streptavidin), amylose (for binding to maltose binding protein or a fusion protein), Ni-NTA (for binding to poly-histidine or poly-histidine tagged proteins) or peptides (such as an antigen).

Diagnosis

In some embodiments, the target polynucleotide is a microRNA (or miRNA). The group of two or more target polynucleotides is preferably a group of two or more miRNAs. Suitable miRNAs for use in diagnosis are well known in the art. For instance, suitable miRNAs are stored on publically available databases (Jiang Q., Wang Y., Hao Y., Juan L., Teng M., Zhang X., Li M., Wang G., Liu Y., (2009) miR2Disease: a manually curated database for microRNA deregulation in human disease. Nucleic Acids Res.).

miRNA(s) can, for example, be used to diagnose or prognose a disease or condition. The disease or condition is preferably cancer, coronary heart disease, cardiovascular disease or sepsis. The disease or condition is more preferably abdominal aortic aneurysm, acute lymphoblastic leukemia (ALL), acute myeloid leukemia (AML), acute myocardial infarction, acute promyelocytic leukemia (APL), adenoma, adrenocortical carcinoma, alcoholic liver disease, Alzheimer's disease, anaplastic thyroid carcinoma (ATC), anxiety disorder, asthma, astrocytoma, atopic dermatitis, autism spectrum disorder (ASD), B-cell chronic lymphocytic leukemia, B-cell lymphoma, Becker muscular dystrophy (BMD), bladder cancer, brain neoplasm, breast cancer, Burkitt lymphoma, cardiac hypertrophy, cardiomyopathy, cardiovascular disease, cerebellar neurodegeneration, cervical cancer, cholangiocarcinoma, cholesteatoma, choriocarcinoma, chronic lymphocytic leukemia, chronic myeloid leukemia, chronic pancreatitis, colon carcinoma, colorectal cancer, congenital heart disease, coronary artery disease, cowden syndrome, dermatomyositis (DM), diabetic nephropathy, diarrhea predominant irritable bowel syndrome, diffuse large B-cell lymphoma, dilated cardiomyopathy, down syndrome (DS), duchenne muscular dystrophy (DMD), endometrial cancer, endometrial endometrioid adenocarcinoma, endometriosis, epithelial ovarian cancer, esophageal cancer, esophagus squamous cell carcinoma, essential thrombocythemia (ET), facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, glomerulosclerosis, hamartoma, HBV-related cirrhosis, HCV infection, head and neck cancer, head and neck squamous cell carcinoma (HNSCC), hearing loss, heart disease, heart failure, hepatitis B, hepatitis C, hepatocellular carcinoma (HCC), hilar cholangiocarcinoma, Hodgkin's lymphoma, homozygous sickle cell disease (HbSS), Huntington's disease (HD), hypertension, hypopharyngeal cancer, inclusion body myositis (IBM), insulinoma, intrahepatic cholangiocarcinoma (ICC), kidney cancer, kidney disease, laryngeal carcinoma, late insomnia (sleep disease), leiomyoma of lung, leukemia, limb-girdle muscular dystrophies types 2A (LGMD2A), lipoma, lung adenocarcinoma, lung cancer, lymphoproliferative disease, malignant lymphoma, malignant melanoma, malignant mesothelioma (MM), mantle cell lymphoma (MCL), medulloblastoma, melanoma, meningioma, metabolic disease, miyoshi myopathy (MM), multiple myeloma (MM), multiple sclerosis, MYC-rearranged lymphoma, myelodysplastic syndrome, myeloproliferative disorder, myocardial infarction, myocardial injury, myoma, nasopharyngeal carcinoma (NPC), nemaline myopathy (NM), nephritis, neuroblastoma (NB), neutrophilia, Niemann-Pick type C (NPC) disease, non-alcoholic fatty liver disease (NAFLD), non-small cell lung cancer (NSCLC), obesity, oral carcinomaosteosarcoma ovarian cancer (OC), pancreatic cancer, pancreatic ductal adenocarcinoma (PDAC), pancreatic neoplasia, panic disease, papillary thyroid carcinoma (PTC), Parkinson's disease, PFV-1 infection, pharyngeal disease, pituitary adenoma, polycystic kidney disease, polycystic liver disease, polycythemia vera (PV), polymyositis (PM), primary biliary cirrhosis (PBC), primary myelofibrosis, prion disease, prostate cancer, psoriasic arthritis, psoriasis, pulmonary hypertension, recurrent ovarian cancer, renal cell carcinoma, renal clear cell carcinoma, retinitis pigmentosa (RP), retinoblastoma, rhabdomyosarcoma, rheumatic heart disease and atrial fibrillation, rheumatoid arthritis, sarcoma, schizophrenia, sepsis, serous ovarian cancer, Sezary syndrome, skin disease, small cell lung cancer, spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis or Waldenstrom macroglobulinemia (WM). Since the multiplex method of the invention may determine the presence of absence of two or more miRNAs, it is possible to prognose or diagnose two or more of any of the diseases listed above.

Apparatus and Conditions

Electrical measurements may be made using standard single channel recording equipment known in the art, for example, as described in Stoddart, D. S., et al., (2009), Proceedings of the National Academy of Sciences of the United States of America 106, p 7702-7707, Lieberman K R et al, J Am Chem Soc. 2010; 132(50):17961-72, and International Application WO-2000/28312. Alternatively, electrical measurements may be made using a multi-channel system, for example as described in WO 2009/077734 and WO 2011/067559.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in WO 2008/102120, WO 2010/122293 or WO 00/28312.

The methods involve measuring the ion current flow through the pore, typically by measurement of a current. Alternatively, the ion flow through the pore may be measured optically, such as disclosed by Heron et al: J. Am. Chem. Soc. 9 Vol. 131, No. 5, 2009. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods may be carried out on a silicon-based array of wells where each array comprises 128, 256, 512, 1024, 2000, 3000, 4000, 6000, 10000, 12000, 15000 or more wells. The methods of the invention may involve the measuring of a current flowing through the pore. Suitable conditions for measuring ionic currents through transmembrane pores are known in the art and disclosed in the Examples. The method is typically carried out with a voltage applied across the membrane and pore. The voltage used is typically from +2 V to −2 V, typically −400 mV to +400 mV.

The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt may be an alkaline earth metal salt such as calcium chloride ($CaCl_2$)). The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of binding/no binding to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The sample and panel of probes may be contacted with the pore on either side of the membrane. The sample and panel of probes are typically contacted with the pore on the same side of the membrane.

The sample and the panel of probes may be contacted with the pore in any order. It is preferred that the sample is contacted with the panel of probes before bringing the sample and probes into contact with the pore. Alternatively, the sample may be contacted with the pore prior to contacting it with the panel of probes, or the panel of probes may be contacted with the pore before contacting the sample with the panel of probes. If the panel of probes is contacted with the pore before the sample is contacted with the pore, it is essential to ensure that sufficient probes remain available for binding to the target polynucleotides (and have not all crossed the membrane through the pore), e.g. by ensuring that a potential is not applied to the transmembrane pore before the probes have bound to the target polynucleotides present in the sample.

Methods of Measuring Concentration

In some embodiments, the method for determining the presence, absence or amount of two or more target polynucleotides may further comprise, particularly for those probes that comprise a quadruplex sequence or a double stranded sequence and a second non-hybridisation region, comparing the different currents flowing through the pore when each probe is bound to its target polynucleotide and unbound. This helps to determine the concentration of the target polynucleotides present in the sample, generally by reference to a calibration curve, use of equilibrium constants or reference to control data. Methods for calculating the concentration are well known in the art. For example, a calibration curve or control data can be used.

The invention also provides a method of determining in a sample the amount of two or more target polynucleotides, the method comprising:

(i) carrying out the method for determining the presence, absence or amount of two or more target polynucleotides; and (ii) for one or more target polynucleotides shown to be present in the sample, comparing the current flowing through the pore with control or reference data for each target polynucleotide and thereby determining the amount of the one two or more target polynucleotides in the sample.

Control or reference data can be generated by conducting control experiments in which known amounts of a target polynucleotide are used to calibrate the assay.

In some embodiments, the method may comprise adding to the sample a calibration polynucleotide and contacting the sample with a panel of probes further comprising a calibration probe that comprises a non-hybridisation region and a hybridisation region that specifically hybridises to the calibration polynucleotide to form a hybridised probe. The calibration probe can be designed in a similar manner as the probes for target polynucleotides described herein. For example, the hybridisation region of the calibration probe may comprise one or more non-natural nucleotides. The one or more non-natural nucleotides present in the hybridisation region of the calibration probe may increase or decrease the duration of the current blockade due to the probe hybridised to the calibration polynucleotide. The increase or decrease in duration of the current blockade is typically such that the proportion of current blockades caused by the calibration probe bound to the calibration polynucleotide occurring within the window of current blockades being measured is increased compared to when the corresponding one or more natural nucleotides are present in the hybridisation region of the calibration probe. The hybridised calibration probe gives rise to a current blockade indicative of that probe. The method may further comprise comparing the frequency or number of current blockades resulting from the calibration probe/calibration polynucleotide interaction with the frequency or number of current blockades resulting from one or more probe/target polynucleotide interactions to determine the amount of the target polynucleotide(s) in the sample. The concentration of the target polynucleotide in the sample may be calculated.

In some embodiments, a calibration polynucleotide having a calibration probe bound thereto may be added to the sample used in a method. The calibration polynucleotide is added to the sample in a known amount, such as at a known concentration. The calibration probe typically binds to the calibration polypeptide under the same conditions that a target polynucleotide binds to its respective probe in the panel of probes.

Kits

In another aspect, the invention also provides a kit for determining in a sample the presence, absence or amount of two or more target polynucleotides. The kit comprises (a) a panel of probes as defined herein and one or more of (b) a membrane anchor, (c) a calibration polynucleotide and (d) a calibration probe. The calibration polynucleotide may be any polynucleotide that can be added to the sample at a known concentration in a method of determining the amount of a target polynucleotide or of target polynucleotides in a sample. Any suitable polynucleotide may be used. Typically the calibration polynucleotide is the same type of polynucleotide as the target polynucleotide. When the target polynucleotide is DNA, the calibration polynucleotide is typically DNA and when the target polynucleotide is RNA, the calibration polynucleotide is typically RNA. For example, the calibration polynucleotide may be a microRNA that is not present or present only at a negligible level in the sample. The calibration polynucleotide may be a naturally occurring polynucleotide or an artificial polynucleotide. The calibration probe is typically a probe as described herein having a hybridisation region that binds to the calibration polynucleotide. The calibration probe maybe present in the panel of probes. Alternatively, the calibration probe may be hybridised to the calibration polynucleotide in the kit. The kit may further comprise a transmembrane pore. Any of the embodiments discussed above with reference to the method of the invention equally apply to the kits.

The kit may further comprise the components of a membrane, such as the phospholipids needed to form an amphiphilic layer, such as a lipid bilayer or tri-block co-polymer.

The kits may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

In another aspect, the invention also provides an apparatus for determining in a sample the presence, absence or amount of two or more target polynucleotides. The apparatus comprises a plurality of pores and a panel of probes of the invention. The apparatus preferably further comprises instructions for carrying out the method of any one of the embodiments. The apparatus may be any conventional apparatus for polynucleotide analysis, such as an array or a chip. Any of the embodiments discussed above with reference to the methods for determining the presence, absence or amount of two or more target polynucleotides are equally applicable to the apparatus of the invention.

The apparatus is preferably set up to carry out any of the embodiments of the method for determining the presence, absence or amount of two or more target polynucleotides.

The apparatus preferably further comprises:

a sensor device that is capable of supporting the membrane and plurality of pores and being operable to perform target polynucleotide characterisation using the pores;

at least one reservoir for holding material for performing the characterisation;

a fluidics system configured to controllably supply material from the at least one reservoir to the sensor device; and a plurality of containers for receiving respective samples, the fluidics system being configured to supply the samples selectively from the containers to the sensor device.

The following Examples illustrate the invention.

Example 1

This example shows how the dwell time for microRNA 150 which is a candidate microRNA marker for sepsis can be adjusted.

Materials

```
DNA Sequences (where mN indicates a 2-O-me-RNA base substitution)
150_4G1C_1Alt (SEQ ID NO: 4 with a cholesterol TEG at the 3' end) Final
concentration = 500 pM
TTTTTTTTTCTTTTTTTTTCTTTTTTTTTTCTTTTTTTTTTCTTTTTTTTTTCTTTTCGG
GGmCAmCTmGGmUAmCAmAGmGGmUTmGGmGA/3CholTEG/

150_4G1C_2Alt (SEQ ID NO: 5 with a cholesterol TEG at the 3' end) Final
concentration = 500 pM
TTTTTTTTTCTTTTTTTTTCTTTTTTTTTTCTTTTTTTTTTCTTTTTTTTTTCTTTTCGG
GGmCACmUGGmUACmAAGmGGTmUGGmGA/3CholTEG/

150_4G1C_3Alt (SEQ ID NO: 6 with a cholesterol TEG at the 3' end) Final
concentration = 500 pM
TTTTTTTTTCTTTTTTTTTCTTTTTTTTTTCTTTTTTTTTTCTTTTTTTTTTCTTTTCGG
GGmCACTmGGTAmCAAGmGGTTmGGGA/3CholTEG/

150_4G1C_4Alt (SEQ ID NO: 7 with a cholesterol TEG at the 3' end) Final
concentration = 500 pM
TTTTTTTTTCTTTTTTTTTCTTTTTTTTTTCTTTTTTTTTTCTTTTTTTTTTCTTTTCGG
GGmCACTGmGTACAmAGGGTmUGGGA/3CholTEG/

150_4G1C_5Alt (SEQ ID NO: 8 with a cholesterol TEG at the 3' end) Final
concentration = 500 pM
TTTTTTTTTCTTTTTTTTTCTTTTTTTTTTCTTTTTTTTTTCTTTTTTTTTTCTTTTCGG
GGmCACTGGmUACAAGmGGTTGGmGA/3CholTEG/

1926T (SEQ ID NO: 9 with a cholesterol TEG at the 3' end) Final
concentration = 500 pM
TTTTTTTTTCTTTTTTTTTCTTTTTTTTTTCTTTTTTTTTTCTTTTTTTTTTCTTTTTTT
TGGCTGTCAATTCATAGGTCAG/3CholTEG/

RNA Sequences miR-150 Final concentration = 500 pM
                                                                (SEQ ID NO: 10)
UCUCCCAACCCUUGUACCAGUG miR-192 Final concentration = 500 pM
                                                                (SEQ ID NO: 11)
CUGACCUAUGAAUUGACAGCC
```

Methods

Six hybridisations were set up in parallel where 10 μM sample miRNAs were hybridised to 10 μM corresponding DNA probe in 50 mM NaCl, 10 mM Tris pH 7.5 using the following protocol:

| | |
|---|---|
| Volume | 100 μl |
| Lid | tracking; 5° C. higher than block temperature; pre-heated |
| Step 1 | 95° C. 2 min 30 sec |
| Step 2 | 5 sec, decrease temperature by −0.1° C. per cycle |
| Step 3 | Go to step 2, repeat 770 times |
| Step 4 | Keep at 4° C. |
| Step 5 | end |

Equal volumes of each 10 μM pre-prepared duplex were added to a low-bind tube and the samples diluted to final working concentration (500 μM) in 500 mM Potassium Chloride, 25 mM K Phosphate buffer pH 8.

Electrical measurements were acquired from single α-hemolysin nanopores inserted in block co-polymer in buffer (600 mM KCl, 25 mM K Phosphate buffer, 75 mM Potassium Ferrocyanide (II), 25 mM Potassium Ferricyanide (III), pH 8.0). After achieving a single pore inserted in the block co-polymer, then buffer (1 mL, 600 mM KCl, 25 mM K Phosphate buffer, 150 mM Potassium Ferrocyanide (II), 150 mM Potassium Ferricyanide (III), pH 8.0) was flowed through the system to remove any excess α-hemolysin nanopores. 500 uL of the pre-hybridised sample was added after ~900 s and the following protocol used to control the potential:

| | Step | | | |
|---|---|---|---|---|
| | 1 | 2 | 3 | Cycles |
| Flip Potential (mV) | 100 | 0 | −120 | 250 |
| Flip duration (s) | 1 | 4 | 20 | |

The protocol detailed above was run for 1 hour and the electrical current for each pore was monitored.

Results

When viewed together the non-natural nucleotides present in the hybridisation region resulted in a clear difference in dwell times between the different duplex variants. All variants produced longer current blockades than the unmodified duplex (labelled X in FIG. 1). From the data there was a trend of an increase in the total number of 2-O-me bases (non-natural nucleotides) leading to longer current blockades. Current blockade duration of a calibration duplex (labelled Y in FIG. 1) was also shown, to demonstrate the tuning of a duplex's dwell time.

Example 2

This example shows how the dwell time for microRNA 182 which is a putative microRNA marker for sepsis can be adjusted.

Materials

```
DNA Sequences (where mN indicates a 2-O-me-RNA base substitution)
182_3T_3G_1Alt (SEQ ID NO: 12 with a cholesterol TEG at the 3' end) Final
concentration = 500 pM
TTTTTTTTTTCTTTTTTTTTTCTTTTTTTTTTCTTTTTTTTTTCTTTTTTTTTTCTTTTTTG
GGmAGmUGmUGmAGmUTmCTmACmCAmUTmGCmCAmAA/3CholTEG/

182_3T_3G_2Alt (SEQ ID NO: 13 with a cholesterol TEG at the 3' end) Final
concentration = 500 pM
TTTTTTTTTTCTTTTTTTTTTCTTTTTTTTTTCTTTTTTTTTTCTTTTTTTTTTCTTTTTTG
GGmAGTmGTmGmAGTmUCTmACCmATTmGCCmAAA/3CholTEG/

182_3T_3G_3Alt (SEQ ID NO: 14 with a cholesterol TEG at the 3' end) Final
concentration = 500 pM
TTTTTTTTTTCTTTTTTTTTTCTTTTTTTTTTCTTTTTTTTTTCTTTTTTTTTTCTTTTTTG
GGmAGTmGmUGAGmUTCTmACCmAmUTGCmCAAA/3CholTEG/

182_3T_3G_4Alt (SEQ ID NO: 15 with a cholesterol TEG at the 3' end) Final
concentration = 500 pM
TTTTTTTTTTCTTTTTTTTTTCTTTTTTTTTTCTTTTTTTTTTCTTTTTTTTTTCTTTTTTG
GGmAGTGTmGAGTTmCTACCmATTGCmCAAA/3CholTEG/

182_3T_3G_5Alt (SEQ ID NO: 16 with a cholesterol TEG at the 3' end) Final
concentration = 500 pM
TTTTTTTTTTCTTTTTTTTTTCTTTTTTTTTTCTTTTTTTTTTCTTTTTTTTTTCTTTTTTG
GGmAGTGTmGAGTTCTmACCATTmGCCAAA/3CholTEG/

1926T (SEQ ID NO: 9 with a cholesterol TEG at the 3' end) Final
concentration = 500 pM
TTTTTTTTTTCTTTTTTTTTTCTTTTTTTTTTCTTTTTTTTTTCTTTTTTTTTTCTTTTTTTT
TGGCTGTCAATTCATAGGTCAG/3CholTEG/

RNA Sequences
miR-182 Final concentration = 500 pM
                                                     (SEQ ID NO: 17)
UUUGGCAAUGGUAGAACUCACACU miR-192 Final concentration = 500 pM
                                                     (SEQ ID NO: 11)
CUGACCUAUGAAUUGACAGCC
```

Methods

Six hybridisations were set up in parallel where 10 µM sample miRNAs were hybridised to 10 µM corresponding DNA probe in 50 mM NaCl, 10 mM Tris pH 7.5 using the following protocol:

| Volume | 100 µl |
|---|---|
| Lid | tracking; 5° C. higher than block temperature; pre-heated |
| Step 1 | 95° C. 2 min 30 sec |
| Step 2 | 5 sec, decrease temperature by −0.1° C. per cycle |
| Step 3 | Go to step 2, repeat 770 times |
| Step 4 | Keep at 4° C. |
| Step 5 | end |

Equal volumes of each 10 µM pre-prepared duplex were added to a low-bind tube and the samples diluted to final working concentration (500 µM) in 500 mM Potassium Chloride, 25 mM Potassium Phosphate buffer pH 8.

Electrical measurements were acquired from single α-hemolysin nanopores inserted in block co-polymer in buffer (600 mM KCl, 25 mM K Phosphate buffer, 75 mM Potassium Ferrocyanide (II), 25 mM Potassium Ferricyanide (III), pH 8.0). After achieving a single pore inserted in the block co-polymer, then buffer (1 mL, 600 mM KCl, 25 mM K Phosphate buffer, 150 mM Potassium Ferrocyanide (II), 150 mM Potassium Ferricyanide (III), pH 8.0) was flowed through the system to remove any excess α-hemolysin. 500 uL of the pre-hybridised sample was added after ~900 s and the following protocol used to control the potential:

| | Step | | | |
|---|---|---|---|---|
| | 1 | 2 | 3 | Cycles |
| Flip Potential (mV) | 100 | 0 | −120 | 250 |
| Flip duration (s) | 1 | 4 | 20 | |

The protocol detailed above was run or our and the electrical current for each pore was monitored.

Results

Figure 2:
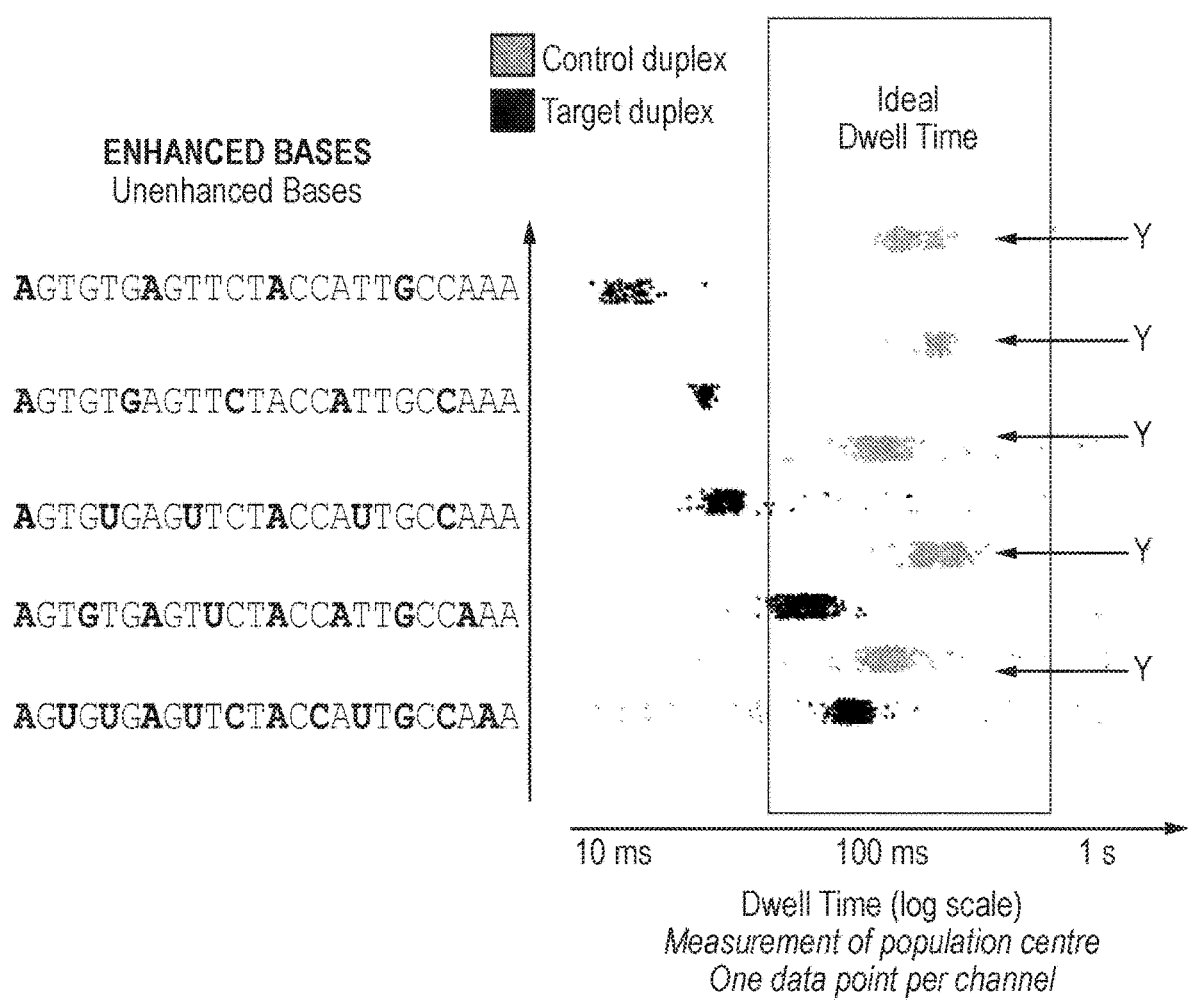
FIG. 2 shows mean current blockade lengths for the calibration duplex (formed with MicroRNA 192, labelled Y) and each microRNA 182 variant and duplexes (SEQ ID NOs: 33-37).

When viewed together the non-natural nucleotides present in the hybridisation region resulted in a clear difference in dwell times between the different duplex variants. From the data there was a trend of an increase in the total number of 2-O-me (non-natural nucleotides) bases leading to longer current blockades (see FIG. 2). The current blockade of a calibration duplex (labelled Y in FIG. 2) was also shown, to demonstrate the tuning of a duplex's dwell time.

Example 3

This example shows how the dwell time for microRNA 342 which is a candidate microRNA marker for sepsis can be adjusted.

Materials

```
DNA Sequences (where mN indicates a 2-O-me-RNA base substitution)
342_3T_3Sp (SEQ ID NO: 18 attached to its 3' end by 3 iSpC3 spacers to
the 5' end of SEQ ID NO: 19 which has a cholesterol TEG at the 3' end)
Final concentration = 500 pM
TTTTTTTTTCTTTTTTTTTCTTTTTTTTTCTTTTTTTTTCTTTTTTTTTCTTTTTT/
iSpC3//iSpC3//iSpC3/TCAATCACAGATAGCACCCCT/3CholTEG/

342_3T_3Sp_all_enh (SEQ ID NO: 18 attached to its 3' end by 3 iSpC3
spacers to the 5' end of SEQ ID NO: 20 which has a cholesterol TEG at
the 3' end) Final concentration = 500 pM
TTTTTTTTTCTTTTTTTTTCTTTTTTTTTCTTTTTTTTTCTTTTTTTTTCTTTTTT/
iSpC3//iSpC3//iSpC3/mTmCmAmAmTmCmAmCmAmGmAmTmAmGmCmAmCmCmCmT/
3CholTEG/

1926T (SEQ ID NO: 9 with a cholesterol TEG at the 3' end) Final
concentration = 500 pM
TTTTTTTTTCTTTTTTTTTCTTTTTTTTTCTTTTTTTTTCTTTTTTTTTCTTTTTTT
TGGCTGTCAATTCATAGGTCAG/3CholTEG/

RNA Sequences
miR-342 Final concentration = 500 pM
                                                         (SEQ ID NO: 21)
AGGGGUGCUAUCUGUGAUUGA miR-192 Final concentration = 500 pM
                                                         (SEQ ID NO: 11)
CUGACCUAUGAAUUGACAGCC
```

Methods

Three hybridisations were set up in parallel where 10 μM sample miRNAs were hybridised to 10 μM corresponding DNA probe in 50 mM NaCl, 10 mM Tris pH 7.5 using the following protocol:

| Volume | 100 μl |
|---|---|
| Lid | tracking; 5° C. higher than block temperature; pre-heated |
| Step 1 | 95° C. 2 min 30 sec |
| Step 2 | 5 sec, decrease temperature by −0.1° C. per cycle |
| Step 3 | Go to step 2, repeat 770 times |
| Step 4 | Keep at 4° C. |
| Step 5 | end |

Equal volumes of each 10 μM pre-prepared duplex were added to a low-bind tube and the samples diluted to final working concentration (500 μM) in 500 mM Potassium Chloride, 25 mM K Phosphate buffer pH 8.

Electrical measurements were acquired from single α-hemolysin nanopores inserted in block co-polymer in buffer (600 mM KCl, 25 mM K Phosphate buffer, 75 mM Potassium Ferrocyanide (II), 25 mM Potassium Ferricyanide (III), pH 8.0). After achieving a single pore inserted in the block co-polymer, then buffer (1 mL, 600 mM KCl, 25 mM K Phosphate buffer, 150 mM Potassium Ferrocyanide (II), 150 mM Potassium Ferricyanide (III), pH 8.0) was flowed through the system to remove any excess α-hemolysin nanopores. 500 uL of the pre-hybridised sample was added after ~900 s and the following protocol used to control the potential.

| | Step | | | |
|---|---|---|---|---|
| | 1 | 2 | 3 | Cycles |
| Flip Potential (mV) | 100 | 0 | −120 | 250 |
| Flip duration (s) | 1 | 4 | 20 | |

The protocol detailed above was run for 1 hour and the electrical current for each pore was monitored.

Results

Figure 3:
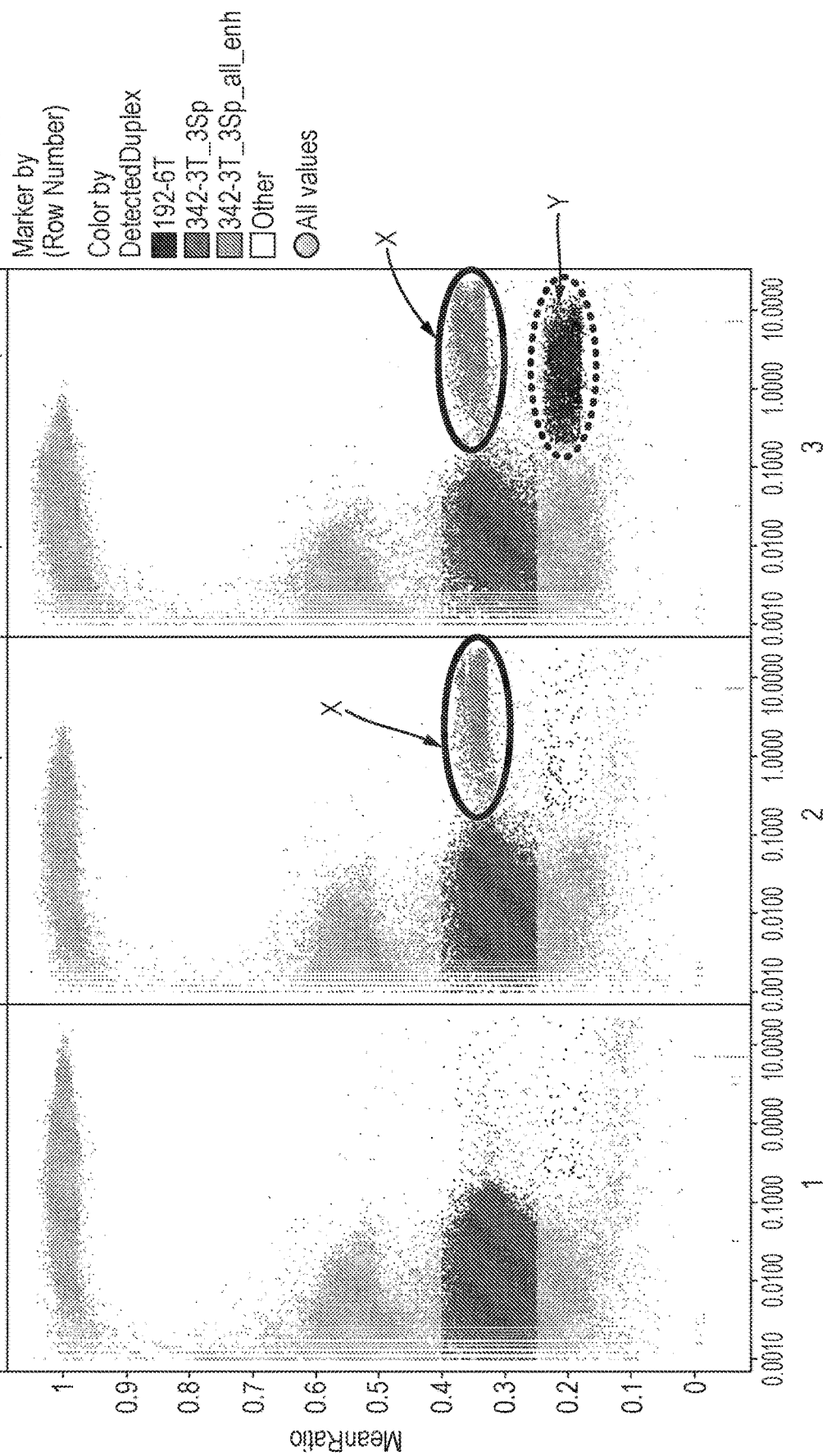
FIG. 3 shows the successful tuning of a miRNA:DNA hybridised duplex. Panel 1 shows the current block ratio and dwell times of unmodified 342_3T_3SP RNA duplex. Panel 2 shows the addition of a dwell tuned 342_3T_3SP duplex to the original sample (342 3T_3Sp_all_enh labeled X). It can be observed that the modification of the hybridisation region (where all of the nucleotides in the hybridisation region were non-natural nucleotides) has moved the mean dwell of the cluster to within a desired window centered around 1 second. Panel 3 shows the addition of a calibration duplex (labeled Y) which is used for comparison between experiments.

FIG. 3 shows that it was possible to successfully tune the dwell time of a miRNA:DNA hybridised duplex blockade so that it clustered in a desired window (which was around 1 second in this example). Panel 1 of FIG. 3 shows the current block ratio and dwell times of unmodified 342_3T_3SP RNA duplex. Panel 2 of FIG. 3 shows the addition of a dwell tuned 342_3T_3SP duplex to the original sample (342 3T_3Sp_all_enh, labelled X). It was observed that the modification of the hybridization region (where all of the nucleotides in the hybridization region were non-natural nucleotides) had moved the mean dwell of the current blockade cluster to within a desired window centered around 1 second. Panel 3 shows the addition of a calibration duplex (labeled Y) which is used to for comparison between experiments.

Example 4

This example shows how five different microRNAs (which are candidate markers of sepsis) were detected using a nanopore. The probes that were used to detect the microRNA had either a) no non-natural nucleotides in the hybridisation region (microRNA 192 and 486), b) all non-natural nucleotides in the hybridisation region (microRNA 342) or c) patterned non-natural nucleotides in the hybridisation region (microRNA 150 and 182).

Materials

```
DNA Sequences (where mN indicates a 2-O-me-RNA base substitution)
182_6T_1Alt (SEQ ID NO: 22 with a cholesterol TEG at the 3' end) Final
concentration = 500 pM
TTTTTTTTTCTTTTTTTTTCTTTTTTTTTCTTTTTTTTTCTTTTTTTTTCTTTTTTTT
TmAGmUGmUGmAGmUTmCTmACmCAmUTmGCmCAmAA/3CholTEG/

192_3_3SP (SEQ ID NO: 18 attached to its 3' end by 3 iSpC3 spacers to the
5' end of SEQ ID NO: 23 which has a cholesterol TEG at the 3' end) Final
concentration = 500 pM
TTTTTTTTTCTTTTTTTTTCTTTTTTTTTCTTTTTTTTTCTTTTTTTTTCTTTTTT/
iSpC3//iSpC3//iSpC3/GGCTGTCAATTCATAGGTCAG/3CholTEG/

342_3T_3SP All_enh (SEQ ID NO: 18 attached to its 3' end by 3 iSpC3 spacers
to the 5' end of SEQ ID NO: 20 which has a cholesterol TEG at the 3' end)
Final concentration = 500 pM
TTTTTTTTTCTTTTTTTTTCTTTTTTTTTCTTTTTTTTTCTTTTTTTTTCTTTTTT/
iSpC3//iSpC3//iSpC3/mTmCmAmAmTmCmAmCmAmGmAmTmAmGmCmAmCmCmCmT/
3CholTEG/

150_4G1C_2A1t (SEQ ID NO: 5 with a cholesterol TEG at the 3' end) Final
concentration = 500 pM
TTTTTTTTTCTTTTTTTTTCTTTTTTTTTCTTTTTTTTTCTTTTTTTTTCTTTTCGG
GGmCACmUGGmUACmAAGmGGTmUGGmGA/3CholTEG/

486_3T_3X (SEQ ID NO: 18 attached at its 3' end to three 1',2'-dideoxyribose
spacers which are attached to the 5' end of SEQ ID NO: 24 which has a cholesterol
TEG at the 3' end) Final concentration = 500 pM
TTTTTTTTTCTTTTTTTTTCTTTTTTTTTCTTTTTTTTTCTTTTTTTTTCTTTTTT/
idSp/idSp/idSp/CTCGGGGCAGCTCAGTACAGGA/3CholTEG/
```

RNA Sequences
hsa-miR-192

(SEQ ID NO: 11)

CUGACCUAUGAAUUGACAGCC hsa-miR-342

(SEQ ID NO: 25)

AAAGGGGUGCUAUCUGUGAUUGA hsa-miR-150

(SEQ ID NO: 10)

UCUCCCAACCCUUGUACCAGUG hsa-miR-182

(SEQ ID NO: 17)

UUUGGCAAUGGUAGAACUCACACU hsa-miR-486

(SEQ ID NO: 26)

UCCUGUACUGAGCUGCCCCGAG

Methods

Five hybridisations were set up in parallel where 10 µM sample miRNAs were hybridised to 10 µM corresponding DNA probe in 50 mM NaCl, 10 mM Tris pH 7.5 using the following protocol:

| Volume | 100 µl |
|---|---|
| Lid | tracking; 5° C. higher than block temperature; pre-heated |
| Step 1 | 95° C. 2 min 30 sec |
| Step 2 | 5 sec, decrease temperature by −0.1° C. per cycle |
| Step 3 | Go to step 2, repeat 770 times |
| Step 4 | Keep at 4° C. |
| Step 5 | end |

Equal volumes of each 10 M pre-prepared duplex were added to a low-bind tube and the samples diluted to a final working concentration (500 µM) in 500 mM Potassium Chloride, 25 mM K Phosphate buffer pH 8.

Electrical measurements were acquired from single α-hemolysin nanopores inserted in block co-polymer in buffer (600 mM KCl, 25 mM K Phosphate buffer, 75 mM Potassium Ferrocyanide (II), 25 mM Potassium Ferricyanide (III), pH 8.0). After achieving a single pore inserted in the block co-polymer, then buffer (1 mL, 600 mM KCl, 25 mM K Phosphate buffer, 150 mM Potassium Ferrocyanide (II), 150 mM Potassium Ferricyanide (III), pH 8.0) was flowed through the system to remove any excess α-hemolysin nanopores. 500 uL of the pre-hybridised sample was added after ~900 s and the following protocol used to control the potential.

| | Step | | | |
|---|---|---|---|---|
| | 1 | 2 | 3 | Cycles |
| Flip Potential (mV) | 100 | 0 | −120 | 250 |
| Flip duration (s) | 1 | 4 | 20 | |

The protocol detailed above was run for 1 hour and the electrical current for each pore was monitored.

Results

Figure 4:
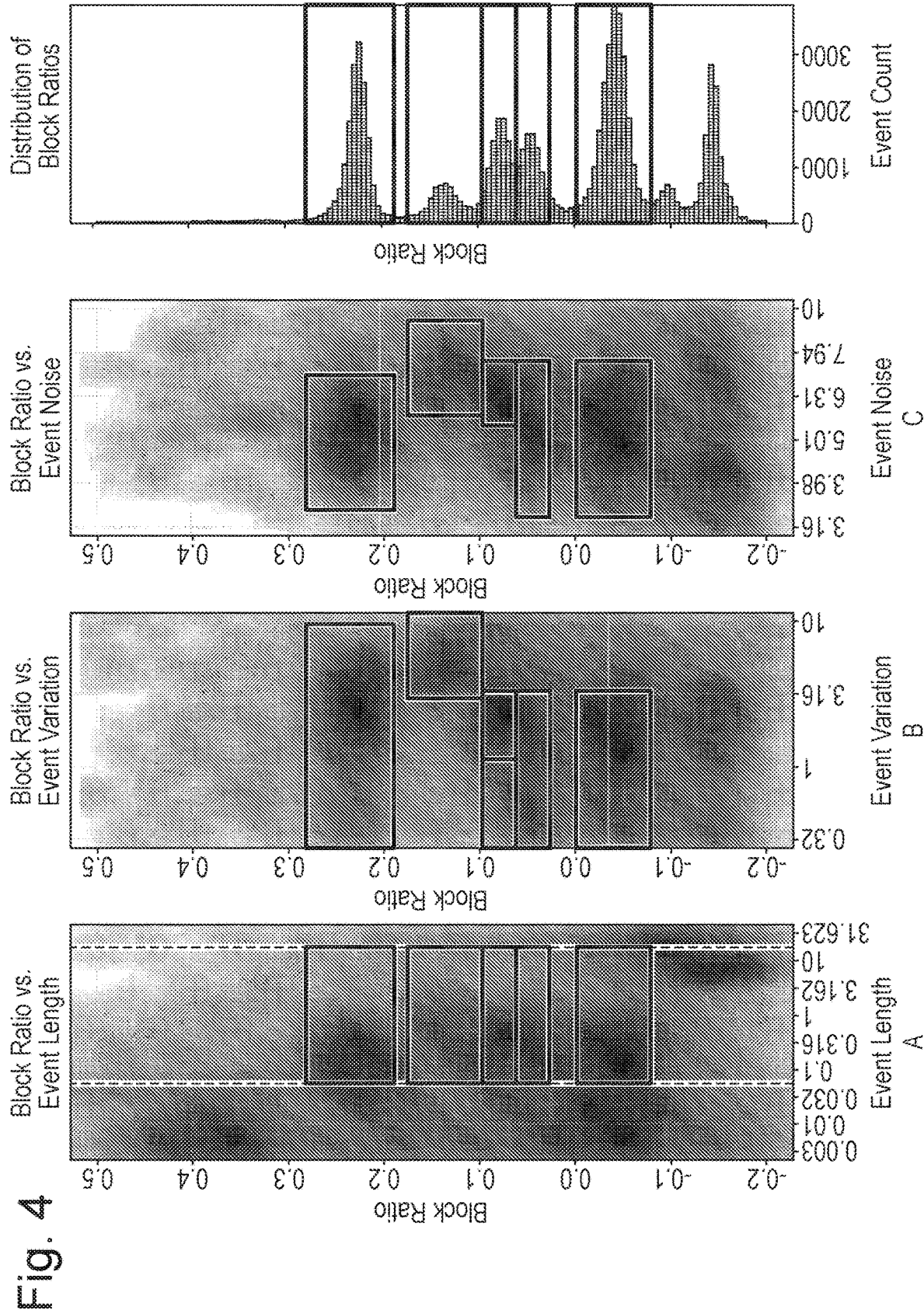
FIG. 4 shows how three metrics were used to determine the identity of a cluster which corresponds to a particular microRNA: Current blockade length (or dwell) (section A); the "variation" or standard deviation (section B); and the current blockade noise (section C).

Here we demonstrate a panel of miRNA and hybridised probes that have been designed to give well separated current blockade clusters. FIG. 4 shows how three metrics were used to determine the identity of a cluster which corresponds to a particular microRNA. Current blockade length (or dwell) (Section A), the "variation" or standard deviation (Section B), and the current blockade noise (Section C). Five clusters were visible corresponding to the 5 duplexes, as highlighted in FIG. 4, In descending order they are: 192-3T_3Sp, 342-3T_3Sp_all_enh, 486-3T_3X, 150_4G_1C_2Alt, 182-6T_1Alt. It can be seen from the first panel that only the current blockades detected within the defined window are measured and put forward for further analysis.

The invention claimed is:

1. A method for determining the presence, absence or amount of two or more target polynucleotides in a sample comprising additional components, the method comprising:
   (i) contacting the sample with a panel of two or more probes under conditions suitable for hybridisation of the target polynucleotides to the probes, wherein:
      (a) each probe comprises a non-hybridisation region and a hybridisation region that specifically hybridises to one of the target polynucleotides to form a hybridised probe;
      (b) the hybridisation region of a probe of the panel comprises one or more non-natural nucleotides; and
      (c) none of the probes comprise a quadruplex-forming sequence:
   (ii) contacting the sample prepared in step (i) with a transmembrane pore through which a single stranded polynucleotide but not a double stranded polynucleotide can pass and applying a potential difference to the transmembrane pore such that the hybridised probes in the sample interact with the pore;
   (iii) measuring current blockades having a duration within a defined dwell time window, wherein:
      (a) the one or more non-natural nucleotides present in the hybridisation region of the probe increase or decrease the duration of the current blockade due to the probe hybridised to its target polynucleotide such that the proportion of current blockades that occur within the window due to the interaction of the hybridised probes with the pore is increased compared to when the corresponding one or more natural nucleotides are present in the hybridisation region; and
      (b) each hybridised probe gives rise to a current blockade indicative of that probe; and
   (iv) correlating the measured current blockades with the probes, thereby determining the presence, absence or amount of the two or more target polynucleotides in the sample.

2. The method according to claim 1, wherein the non-hybridisation regions of at least two of the probes in the panel are different from each other and the method comprises individually determining the presence or absence of the target polynucleotides that hybridise with each one of the at least two probes.

3. The method according to claim 1, wherein each of the probes in the panel comprises a unique non-hybridisation region.

4. The method according to claim 1, wherein the non-natural nucleotide comprises a modified sugar.

5. The method according to claim 1, wherein the non-natural nucleotide comprises a modified nucleobase.

6. The method according to claim 1, wherein at least one of the hybridisation regions comprises one or more instances of ZxNy and/or NyZx where Z is a non-natural nucleotide and N is a natural nucleotide which is complementary to one of the nucleotides in the target polynucleotide, X is 1, 2, 3, 4 or 5 and Y is 1, 2, 3, 4 or 5.

7. The method according to claim 5, wherein in at least one of the probes the non-hybridisation region is 5' to the hybridisation region.

8. The method according to claim 1, wherein in at least one of the probes the hybridisation region is at the 3' end of the probe.

9. The method according to claim 1, wherein the probe further comprises a second non-hybridisation region and either a second hybridisation region or a double stranded region, wherein the first and second non-hybridisation regions are separated by the first or second hybridisation region or the double-stranded region.

10. The method according to claim 1, wherein the non-hybridisation region comprises a polymer and wherein the polymer is a polynucleotide, a polypeptide, a polyethylene glycol (PEG) or a polysaccharide.

11. The method according to claim 1, wherein one or more of the probes further comprises an anchor that allows it to be coupled to the membrane.

12. The method according to claim 1, wherein substantially all of the current blockades due to the interaction of the hybridised probes with the pore occur within the window.

13. The method according to claim 1, wherein the majority of current blockades that occur outside the window are due to the additional components in the sample and wherein the additional components comprise one or more of folded and unfolded proteins, peptides, carbohydrates, short polymers and cell debris.

14. The method according to claim 1, wherein the window is defined as containing current blockades of between 0.01 and 10 seconds.

15. The method according to claim 1, wherein the durations of the current blockades caused by at least two of the probes hybridised to their respective target polynucleotides are within one second or less of each other.

16. The method according to claim 1, wherein at least one of the polynucleotides is a siRNA or microRNA.

17. The method according to claim 1, wherein the method comprises quantifying one or more of the target polynucleotides present in the sample.

18. The method according to claim 1, wherein the size of the transmembrane potential is chosen to optimise the duration of the current blockades caused by probes that have hybridised to their respective target polynucleotides.

19. A method for determining the presence, absence or amount of two or more target polynucleotides in a sample comprising additional components, the method comprising:
   (i) contacting the sample with a panel of two or more probes under conditions suitable for hybridisation of the target polynucleotides to the probes, wherein:
      (a) each probe comprises a non-hybridisation region and a hybridisation region that specifically hybridises to one of the target polynucleotides to form a hybridised probe; and
      (b) the hybridisation region of a probe of the panel comprises one or more non-natural nucleotides; and
      (c) the sample comprises a known amount of a calibration probe hybridised to a calibration polynucleotide or step (i) further comprises adding a known amount of a calibration polynucleotide to the sample and contacting the sample with a calibration probe under conditions suitable for hybridisation of the calibration polynucleotide to the calibration probe, wherein the calibration probe comprises a hybridisation region that specifically hybridises to the calibration polynucleotide and a non-hybridisation region that gives rise to a current blockade indicative of the calibration probe; and
   (ii) contacting the sample prepared in step (i) with a transmembrane pore through which a single stranded polynucleotide but not a double stranded polynucleotide can pass and applying a potential difference to the transmembrane pore such that the hybridised probes in the sample interact with the pore;
   (iii) measuring current blockades having a duration within a defined dwell time window, wherein:

(a) the one or more non-natural nucleotides present in the hybridisation region of the probe increase or decrease the duration of the current blockade due to the probe hybridised to its target polynucleotide such that the proportion of current blockades that occur within the window due to the interaction of the hybridised probes with the pore is increased compared to when the corresponding one or more natural nucleotides are present in the hybridisation region; and (b) each hybridised probe gives rise to a current blockade indicative of that probe;

(iv) correlating the measured current blockades with the probes, thereby determining the presence, absence or amount of the two or more target polynucleotides in the sample (v) comparing the frequency of current blockades resulting from the interaction of one or more probes hybridised to target polynucleotides to the frequency of current blockades resulting from the interaction of the hybridised calibration probe to determine the concentration of one or more of the target polynucleotides.

20. The method according to claim 19, wherein the hybridisation region of the calibration probe comprises one or more non-natural nucleotides which increase or decrease the duration of the current blockade due to the calibration probe hybridised to the calibration polynucleotide such that the proportion of current blockades that occur within the window due to the interaction of the hybridised calibration probe with the pore is increased compared to when the corresponding one or more natural nucleotides are present in the hybridisation region.

* * * * *

UNITED STATES PATENT AND TRADEMARK OFFICE
CERTIFICATE OF CORRECTION

| | | |
|---|---|---|
| PATENT NO. | : 11,390,910 B2 | Page 1 of 1 |
| APPLICATION NO. | : 16/343580 | |
| DATED | : July 19, 2022 | |
| INVENTOR(S) | : Nicholas Smith et al. | |

It is certified that error appears in the above-identified patent and that said Letters Patent is hereby corrected as shown below:

On the Title Page

Item (30):
"(30) Foreign Application Priority Data
Oct. 21. 2016 (GB)..........1617886"

Should be:
—(30) Foreign Application Priority Data
Oct. 21. 2016 (GB)..........1617886.5—

In the Claims

At Column 77, Claim 7, Line 59:
"7. The method according to claim 5, wherein in at least"

Should be:
—7. The method according to claim 1, wherein in at least—

Signed and Sealed this
Thirteenth Day of September, 2022

Katherine Kelly Vidal
*Director of the United States Patent and Trademark Office*